US011339191B2

(12) United States Patent
Laconde et al.

(10) Patent No.: US 11,339,191 B2
(45) Date of Patent: May 24, 2022

(54) STAPLED PEPTIDES AND USES THEREOF

(71) Applicants: Universite de Montpellier, Montpellier (FR); Centre National de la Recherche Scientifique (CNRS), Paris (FR); Centre Hospitalier Universitaire de Montpellier, Montpellier (FR); Institut National de la Sante et de la Recherche Medicale (INSERM), Paris (FR); Ecole Nationale Superieure de Chimie de Montpellier—ENSCM, Montpellier (FR)

(72) Inventors: Guillaume Laconde, Montpellier (FR); Muriel Amblard-Caussil, Saint Vincent de Barbeyrargues (FR); Jean Martinez, Caux (FR); Christian Jorgensen, Lattes (FR); Florence Apparailly-Sechan, Montpellier (FR); Isabelle Duroux-Richard, Vailhauques (FR)

(73) Assignees: Universite de Montpellier, Montpellier (FR); Centre National de la Recherche Scientifique (CNRS), Paris (FR)

( * ) Notice: Subject to any disclaimer, the term of this patent is extended or adjusted under 35 U.S.C. 154(b) by 301 days.

(21) Appl. No.: 16/472,298

(22) PCT Filed: Dec. 22, 2017

(86) PCT No.: PCT/EP2017/084309
§ 371 (c)(1),
(2) Date: Jun. 21, 2019

(87) PCT Pub. No.: WO2018/115400
PCT Pub. Date: Jun. 28, 2018

(65) Prior Publication Data
US 2021/0130405 A1  May 6, 2021

(30) Foreign Application Priority Data

Dec. 22, 2016 (EP) .................................. 16306788

(51) Int. Cl.
*C07K 7/08* (2006.01)
*A61K 38/00* (2006.01)
*A61K 45/06* (2006.01)

(52) U.S. Cl.
CPC ................ *C07K 7/08* (2013.01); *A61K 38/00* (2013.01); *A61K 45/06* (2013.01)

(58) Field of Classification Search
CPC ........... C07K 7/08; A61K 38/00; A61K 45/06
See application file for complete search history.

(56) References Cited

PUBLICATIONS

Benosman et al., *Interleukin-1 Receptor-Associated Kinase-2 (IRAK2) Is a Critical Mediator of Endoplasmic Reticulum (ER) Stress Signaling*, 8(5) PLOS ONE (May 1-12, 2013).
(Continued)

*Primary Examiner* — Kevin S Orwig
*Assistant Examiner* — John Michael Cronin
(74) *Attorney, Agent, or Firm* — Panitch Schwarze Belisario & Nadel LLP; Erin M. Dunston

(57) ABSTRACT

The present invention relates to peptidomimetic macrocycles comprising at least one macrocycle-forming linker and an amino acid sequence chosen from the group consisting of: i) an amino acid sequence with at least about 50%, 60%, 70%, 80%, 90%, or 95% sequence identity to a human sequence IRAK2 54-71 (SEQ ID No1) and 100% identity with the amino acids in the positions 5-6, 9-11, 14-15 or ii) an amino acid sequence with at least about 50%, 60%, 70, 80%, 90%, or 95% sequence identity to a human sequence IRAKM 66-83 (SEQ ID No2) and 100% identity with the amino acids in the positions 5-6, 9-11, 13-14, wherein the peptidomimetic macrocycle comprises an a-helix and at least two natural or two non-natural amino acids crosslinked (Continued)

by a macrocycle-forming linker. It also concerns method of preparation of said peptidomimetic macrocycles and uses thereof, pharmaceutical composition and uses thereof, in particular as inhibitors of inflammatory pathways.

19 Claims, 7 Drawing Sheets

Specification includes a Sequence Listing.

(56) References Cited

PUBLICATIONS

Biswas et al., *Endotoxin tolerance: new mechanisms, molecules and clinical significance*, 30(10) Trends in Immunology 475-487 (Oct. 2009).

Chaudhary et al., *Recent Advances in the Discovery of Small Molecule Inhibitors of Ingterleukin-1 Receptor-Associated Kinase 4 (IRAK4) as a Therapeutic Target for Inflammation and Oncology Disorders*, 58 J. Med. Chem. 96-110 (2015).

Du et al., *The structure function of the death domain of human IRAK-M*, 12(77) Cell Communication and Signaling 1-10 (2014).

Escoll et al., *Rapid up-regulation of IRAK-M expression following a second endotoxin challenge in human monocytes and in monocytes isolated from septic patients*, 311 (2) Biochemical and Biophysical Research Communications 465-472 (2003).

Grubbs et al., *Ring-Closing Metathesis and Related Processes in Organic Synthesis*, 28(11) Accounts of Chemical Research 446-452 (1995).

Guerlavais et al., *Chapter Twenty-One. Advancements in Stapled Peptide Drug Discovery & development*, 49 Annual Reports in Medicinal Chemistry 331-345 (Oct. 2014).

Jain et al., *IL-1 receptor associated kinase signaling and is role in inflammation, cancer progression, and therapy resistance*, 5(553) Frontiers in Immunology (Nov. 1-8, 2014).

Kawagoe et al., *Sequential control of Toll-like receptor-dependent response by IRAK1 and IRAK2*, 9(6) Nature Immunology 684-691 (Jun. 2008).

Lau et al., *Peptide stapling techniques based on different macrocyclisation chemistries*, 44 Chemical Society Reviews 91-102 (2015).

Lau et al., *Peptide stapling techniques based on different macrocyclisation chemistries*, 00 Chemical Society Reviews 1-12 (2014).

Lin et al., *Helical assembly in the MyD88-IRAK4-IRAK2 complex in TLR/IL-1R signaling*, 465 Nature 885-891 (Jun. 17, 2010) with Supplementary Information.

Needleman et al., *A General Method Applicable to the Search for Similarities in the Amino Acid Sequence of Two Proteins*, 48(3) Journal of Molecular Biology 445-453 (Mar. 1970).

O'Neill et al., *The Family of Five: TIR-domain-containing adaptors in Toll-like receptor signalling*, 7(5) Nature Reviews Immunology 353-364 (May 2007).

Pearson et al., *Improved tools for biological sequence comparison*, 85(8) Proc. Natl. Acad. Sci. USA 2444-2448 (Apr. 1988).

Peryshkov et al., *Z-Selective Olefin Metathesis Reactions Promoted by Tungsten Oxo Alkylidene Complexes*, 133(51) Journal of The American Chemical Society 20754-20757 (Dec. 28, 2011).

Smith et al., *Overlapping Genes and Information Theory*, 91(2) Journal of Theoretical Biology 379-380 (Jul. 1981).

Walensky et al., *Hydrocarbon-Stapled Peptides: Principles, Practice, and Progress*, 57(15) Journal of Medicinal Chemistry 6275-6288 (Aug. 2014).

Yu et al., *Synthesis of macrocyclic natural products by catalyst-controlled stereoselective ring-closing metathesis*, 479(7371) Nature 88-93 (Nov. 2011).

Zhou et al., *IRAK-M mediates Toll-like receptor/IL-1R-induced NFKB activation and cytokine production*, 32(4) The EMBO Journal 583-596 (Feb. 2013).

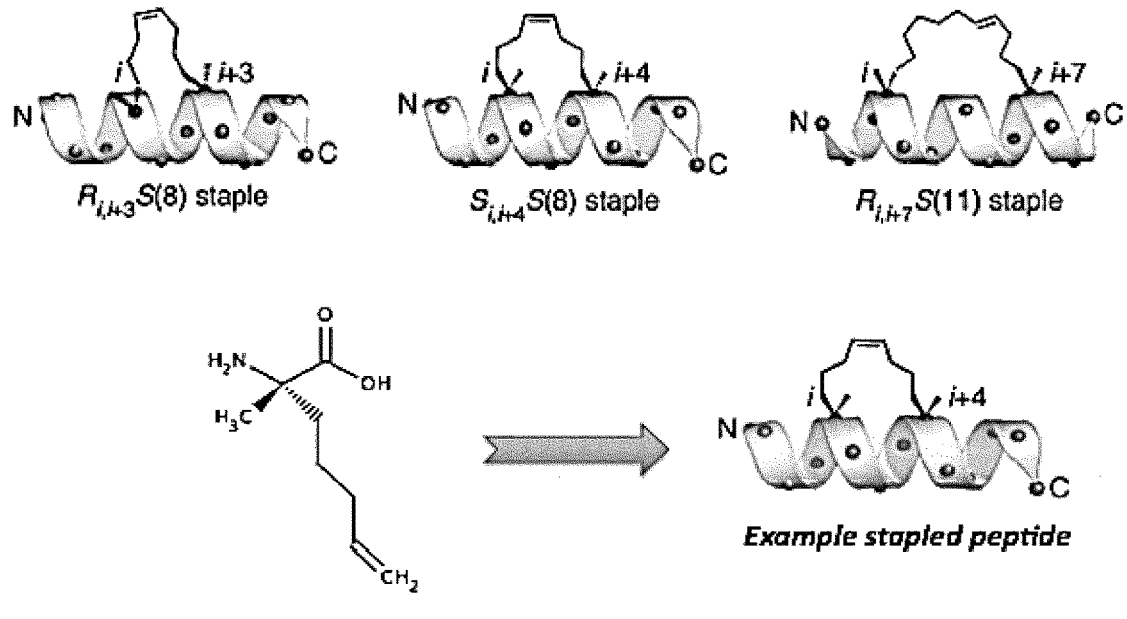

FIGURE 2 A

|  |  | 1 | 2 | 3 | 4 | 5 | 6 | 7 | 8 | 9 | 10 | 11 | 12 | 13 | 14 | 15 | 16 | 17 | 18 | Amino acids positions |
|---|---|---|---|---|---|---|---|---|---|---|---|---|---|---|---|---|---|---|---|---|
|  | IRAK2 54-71 | V | S | I | T | R | E | L | L | W | W | W | G | M | R | Q | A | T | V |  |
|  | IRAKM 66-83 | K | S | G | T | R | E | L | L | W | S | W | A | Q | K | N | K | T | I |  |
| SEQ ID N°3 | IRAK2-S1 JMV6645 |  |  |  | S5 | R | E | L | S5 | W | W | W | G | B | R | Q | A |  |  |  |
| SEQ ID N°4 | IRAK2 S2 JMV6646 |  |  |  | R | R | E | L | S5 | W | W | W | S5 | B | R | Q | A |  |  |  |
| SEQ ID N°5 | IRAKMS1 JMV6647 | K | S | G | S5 | R | E | L | S5 | W | S | W | A | Q | K |  |  |  |  |  |
| SEQ ID N°6 | IRAKM S2 JMV6648 |  |  |  | R | R | E | L | S5 | W | S | W | S5 | Q | K |  |  |  |  |  |
| SEQ ID N°10 | IRAK2-JMV6650 | V | S | I | S5 | R | E | L | S5 | W | W | W | G | B | R | Q | A | T | V |  |
| SEQ ID N°11 | IRAKM-JMV6649 | K | S | G | S5 | R | E | L | S5 | W | S | W | A | Q | K | N | K | T | I |  |
| SEQ ID N°12 | IRAK2-JMV6651 |  |  |  | K | R | E | L | D | W | W | W | G | B | R | Q | A |  |  |  |
| SEQ ID N°13 | IRAK2-JMV6652 | V | S | I | K | R | E | L | D | W | W | W | G | B | R | Q | A | T | V |  |
| SEQ ID N°14 | IRAKM-JMV6653 | K | S | G | K | R | E | L | D | W | S | W | A | Q | K |  |  |  |  |  |
| SEQ ID N°15 | IRAKM-JMV6654 | K | S | G | K | R | E | L | D | W | S | W | A | Q | K | N | K | T | I |  |

FIGURE 2 B

A
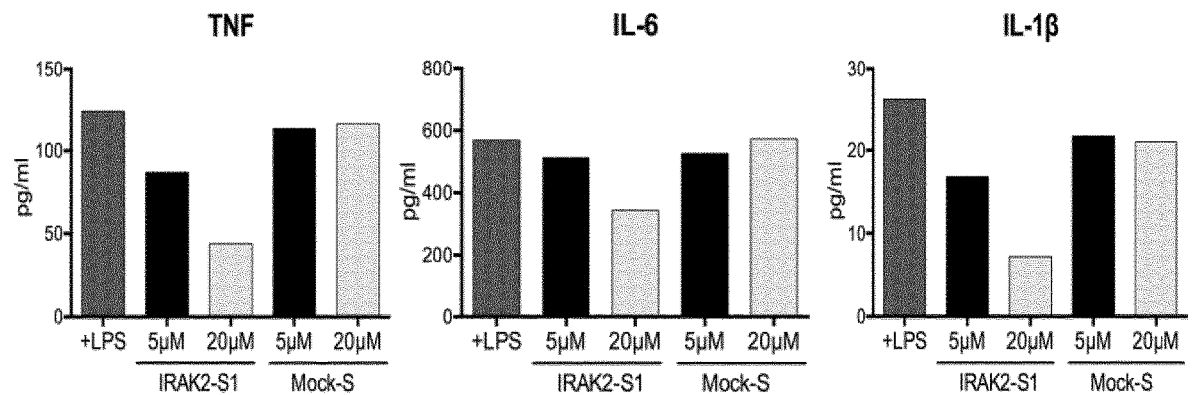
B
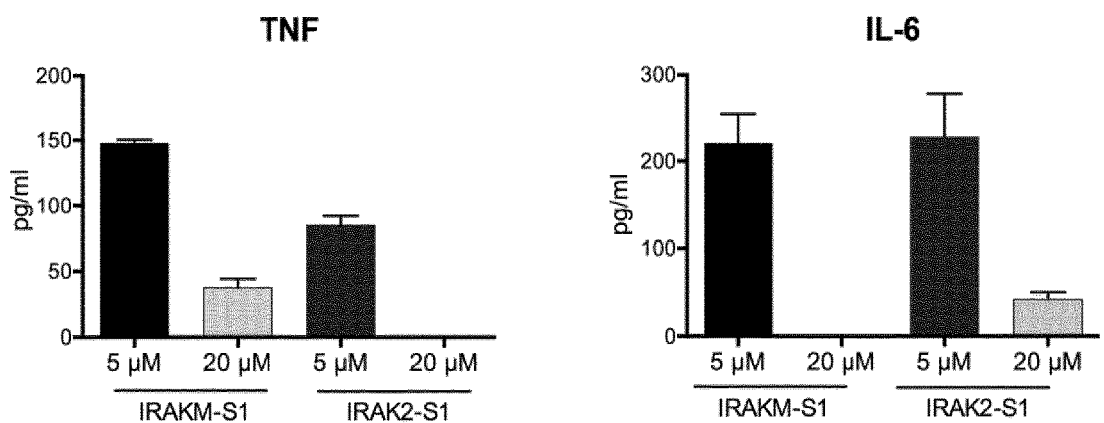
FIGURE 5
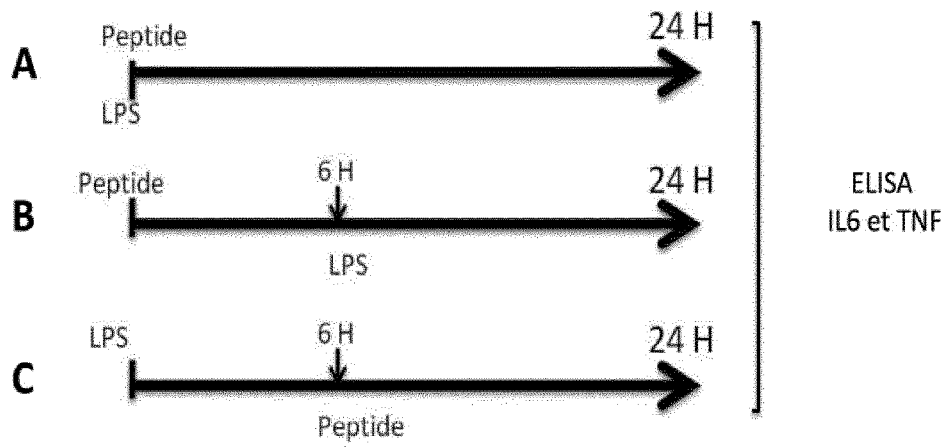
FIGURE 6

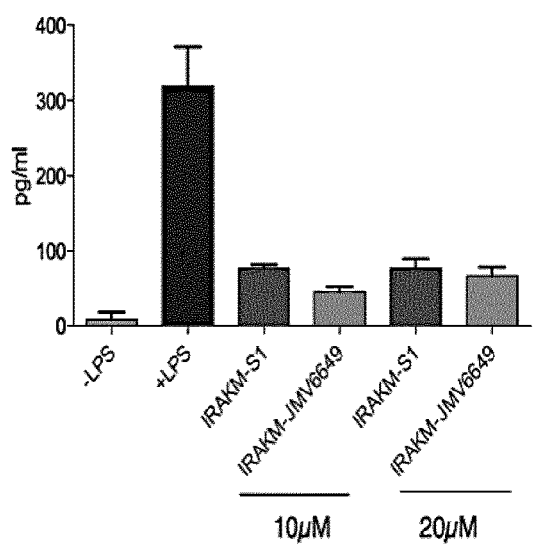
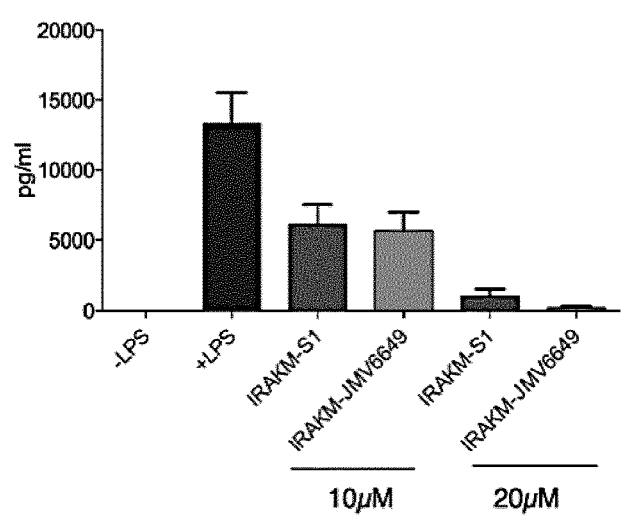
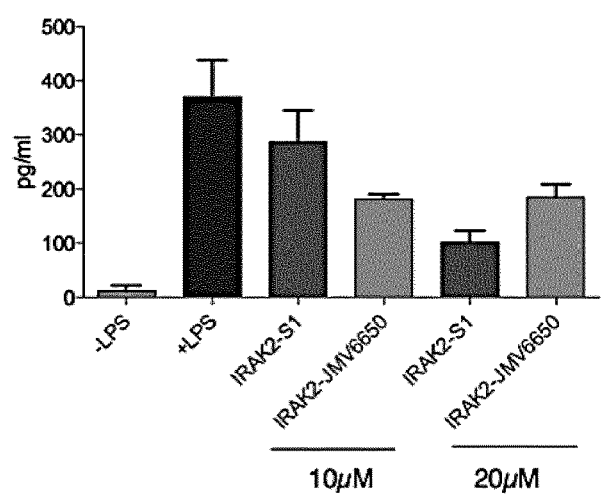
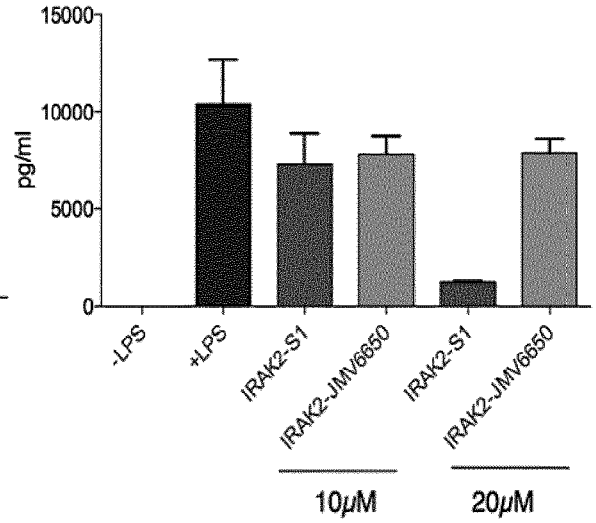
FIGURE 8 ns and thus interfere with the 'Myddosome' assembly and downstream production of pro-inflammatory mediators.

SEQUENCE LISTING

```
<160> NUMBER OF SEQ ID NOS: 15

<210> SEQ ID NO 1
<211> LENGTH: 18
<212> TYPE: PRT
<213> ORGANISM: artificial
<220> FEATURE:
<223> OTHER INFORMATION: linear peptide IRAK2 54-71

<400> SEQUENCE: 1

Val Ser Ile Thr Arg Glu Leu Leu Trp Trp Trp Gly Met Arg Gln Ala
1               5                   10                  15

Thr Val

<210> SEQ ID NO 2
<211> LENGTH: 18
<212> TYPE: PRT
<213> ORGANISM: artificial
<220> FEATURE:
<223> OTHER INFORMATION: linear peptide IRAKM 66-83

<400> SEQUENCE: 2

Lys Ser Gly Thr Arg Glu Leu Leu Trp Ser Trp Ala Gln Lys Asn Lys
1               5                   10                  15

Thr Ile

<210> SEQ ID NO 3
<211> LENGTH: 13
<212> TYPE: PRT
<213> ORGANISM: artificial
<220> FEATURE:
<223> OTHER INFORMATION: stapled peptide IRAK2 S1 (JMV6645)
<220> FEATURE:
<221> NAME/KEY: BINDING
<222> LOCATION: (1)..(5)
<220> FEATURE:
<221> NAME/KEY: MOD_RES
<222> LOCATION: (1)..(1)
<223> OTHER INFORMATION: Xaa is a (S)-2-(4'-pentenyl)alanine
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: Xaa is a (S)-2-(4'-pentenyl)alanine
<220> FEATURE:
<221> NAME/KEY: MOD_RES
<222> LOCATION: (10)..(10)
<223> OTHER INFORMATION: Xaa is Nle
```

```
<220> FEATURE:
<221> NAME/KEY: MOD_RES
<222> LOCATION: (13)..(13)
<223> OTHER INFORMATION: AMIDATION

<400> SEQUENCE: 3

Xaa Arg Glu Leu Xaa Trp Trp Trp Gly Xaa Arg Gln Ala
1               5                   10

<210> SEQ ID NO 4
<211> LENGTH: 13
<212> TYPE: PRT
<213> ORGANISM: artificial
<220> FEATURE:
<223> OTHER INFORMATION: stapled peptide IRAK2 S2 (JMV6646)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (5)..(9)
<220> FEATURE:
<221> NAME/KEY: MOD_RES
<222> LOCATION: (5)..(5)
<223> OTHER INFORMATION: Xaa is a (S)-2-(4'-pentenyl)alanine
<220> FEATURE:
<221> NAME/KEY: MOD_RES
<222> LOCATION: (9)..(9)
<223> OTHER INFORMATION: Xaa is a (S)-2-(4'-pentenyl)alanine
<220> FEATURE:
<221> NAME/KEY: MOD_RES
<222> LOCATION: (10)..(10)
<223> OTHER INFORMATION: Xaa is Nle
<220> FEATURE:
<221> NAME/KEY: MOD_RES
<222> LOCATION: (13)..(13)
<223> OTHER INFORMATION: AMIDATION

<400> SEQUENCE: 4

Arg Arg Glu Leu Xaa Trp Trp Trp Xaa Xaa Arg Gln Ala
1               5                   10

<210> SEQ ID NO 5
<211> LENGTH: 14
<212> TYPE: PRT
<213> ORGANISM: artificial
<220> FEATURE:
<223> OTHER INFORMATION: stapled peptide IRAKM S1 (JMV6647)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (4)..(4)
<223> OTHER INFORMATION: Xaa is a (S)-2-(4'-pentenyl)alanine
<220> FEATURE:
<221> NAME/KEY: MOD_RES
<222> LOCATION: (8)..(8)
<223> OTHER INFORMATION: Xaa is a (S)-2-(4'-pentenyl)alanine
<220> FEATURE:
<221> NAME/KEY: MOD_RES
<222> LOCATION: (14)..(14)
<223> OTHER INFORMATION: AMIDATION

<400> SEQUENCE: 5

Lys Ser Gly Xaa Arg Glu Leu Xaa Trp Ser Trp Ala Gln Lys
1               5                   10
```

```
<210> SEQ ID NO 6
<211> LENGTH: 11
<212> TYPE: PRT
<213> ORGANISM: artificial
<220> FEATURE:
<223> OTHER INFORMATION: stapled peptide IRAKM S2 (JMV6648)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (5)..(9)
<220> FEATURE:
<221> NAME/KEY: MOD_RES
<222> LOCATION: (5)..(5)
<223> OTHER INFORMATION: Xaa is a (S)-2-(4'-pentenyl)alanine
<220> FEATURE:
<221> NAME/KEY: MOD_RES
<222> LOCATION: (9)..(9)
<223> OTHER INFORMATION: Xaa is a (S)-2-(4'-pentenyl)alanine
<220> FEATURE:
<221> NAME/KEY: MOD_RES
<222> LOCATION: (11)..(11)
<223> OTHER INFORMATION: AMIDATION

<400> SEQUENCE: 6

Arg Arg Glu Leu Xaa Trp Ser Trp Xaa Gln Lys
1               5                   10

<210> SEQ ID NO 7
<211> LENGTH: 13
<212> TYPE: PRT
<213> ORGANISM: artificial
<220> FEATURE:
<223> OTHER INFORMATION: linear peptide IRAK2 Li
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: Xaa is Nle
<220> FEATURE:
<221> NAME/KEY: MOD_RES
<222> LOCATION: (13)..(13)
<223> OTHER INFORMATION: AMIDATION

<400> SEQUENCE: 7

Arg Arg Glu Leu Leu Trp Trp Trp Gly Xaa Arg Gln Ala
1               5                   10

<210> SEQ ID NO 8
<211> LENGTH: 11
<212> TYPE: PRT
<213> ORGANISM: artificial
<220> FEATURE:
<223> OTHER INFORMATION: linear peptide IRAKM Li
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: AMIDATION

<400> SEQUENCE: 8

Arg Arg Glu Leu Leu Trp Ser Trp Ala Gln Lys
1               5                   10

<210> SEQ ID NO 9
```

```
<211> LENGTH: 12
<212> TYPE: PRT
<213> ORGANISM: artificial
<220> FEATURE:
<223> OTHER INFORMATION: stapled peptide Mock-S
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (4)..(4)
<223> OTHER INFORMATION: Xaa is a (S)-2-(4'-pentenyl)alanine
<220> FEATURE:
<221> NAME/KEY: MOD_RES
<222> LOCATION: (8)..(8)
<223> OTHER INFORMATION: Xaa is a (S)-2-(4'-pentenyl)alanine
<220> FEATURE:
<221> NAME/KEY: MOD_RES
<222> LOCATION: (12)..(12)
<223> OTHER INFORMATION: AMIDATION

<400> SEQUENCE: 9

Ile Thr Phe Xaa Asn Leu Leu Xaa Tyr Tyr Gly Pro
1               5                   10

<210> SEQ ID NO 10
<211> LENGTH: 18
<212> TYPE: PRT
<213> ORGANISM: artificial
<220> FEATURE:
<223> OTHER INFORMATION: stapled peptide IRAK2 (JMV6650)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (4)..(4)
<223> OTHER INFORMATION: Xaa is a (S)-2-(4'-pentenyl)alanine
<220> FEATURE:
<221> NAME/KEY: MOD_RES
<222> LOCATION: (8)..(8)
<223> OTHER INFORMATION: Xaa is a (S)-2-(4'-pentenyl)alanine
<220> FEATURE:
<221> NAME/KEY: MOD_RES
<222> LOCATION: (13)..(13)
<223> OTHER INFORMATION: Xaa is Nle
<220> FEATURE:
<221> NAME/KEY: MOD_RES
<222> LOCATION: (18)..(18)
<223> OTHER INFORMATION: AMIDATION

<400> SEQUENCE: 10

Val Ser Ile Xaa Arg Glu Leu Xaa Trp Trp Trp Gly Xaa Arg Gln Ala
1               5                   10                  15

Thr Val

<210> SEQ ID NO 11
<211> LENGTH: 18
<212> TYPE: PRT
<213> ORGANISM: artificial
<220> FEATURE:
<223> OTHER INFORMATION: stapled peptide IRAKM (JMV6649)
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: BINDING
<222> LOCATION: (4)..(8)
<220> FEATURE:
<221> NAME/KEY: MOD_RES
<222> LOCATION: (4)..(4)
<223> OTHER INFORMATION: Xaa is a (S)-2-(4'-pentenyl)alanine
<220> FEATURE:
<221> NAME/KEY: MOD_RES
<222> LOCATION: (8)..(8)
<223> OTHER INFORMATION: Xaa is a (S)-2-(4'-pentenyl)alanine
<220> FEATURE:
<221> NAME/KEY: MOD_RES
<222> LOCATION: (18)..(18)
<223> OTHER INFORMATION: AMIDATION

<400> SEQUENCE: 11

Lys Ser Gly Xaa Arg Glu Leu Xaa Trp Ser Trp Ala Gln Lys Asn Lys
1               5                   10                  15

Thr Ile

<210> SEQ ID NO 12
<211> LENGTH: 13
<212> TYPE: PRT
<213> ORGANISM: artificial
<220> FEATURE:
<223> OTHER INFORMATION: stapled peptide IRAK2 (JMV6651)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (1)..(5)
<220> FEATURE:
<221> NAME/KEY: MOD_RES
<222> LOCATION: (10)..(10)
<223> OTHER INFORMATION: Xaa is Nle
<220> FEATURE:
<221> NAME/KEY: MOD_RES
<222> LOCATION: (13)..(13)
<223> OTHER INFORMATION: AMIDATION

<400> SEQUENCE: 12

Lys Arg Glu Leu Asp Trp Trp Trp Gly Xaa Arg Gln Ala
1               5                   10

<210> SEQ ID NO 13
<211> LENGTH: 18
<212> TYPE: PRT
<213> ORGANISM: artificial
<220> FEATURE:
<223> OTHER INFORMATION: stapled peptide IRAK2 (JMV6652)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (13)..(13)
<223> OTHER INFORMATION: Xaa is Nle
<220> FEATURE:
<221> NAME/KEY: MOD_RES
<222> LOCATION: (18)..(18)
<223> OTHER INFORMATION: AMIDATION

<400> SEQUENCE: 13

Val Ser Ile Lys Arg Glu Leu Asp Trp Trp Trp Gly Xaa Arg Gln Ala
1               5                   10                  15
```

Thr Val

```
<210> SEQ ID NO 14
<211> LENGTH: 14
<212> TYPE: PRT
<213> ORGANISM: artificial
<220> FEATURE:
<223> OTHER INFORMATION: stapled peptide IRAKM (JMV6653)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (14)..(14)
<223> OTHER INFORMATION: AMIDATION

<400> SEQUENCE: 14

Lys Ser Gly Lys Arg Glu Leu Asp Trp Ser Trp Ala Gln Lys
1               5                   10

<210> SEQ ID NO 15
<211> LENGTH: 18
<212> TYPE: PRT
<213> ORGANISM: artificial
<220> FEATURE:
<223> OTHER INFORMATION: stapled peptide IRAKM (JMV6654)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: BINDING
<222> LOCATION: (4)..(8)
<220> FEATURE:
<221> NAME/KEY: MOD_RES
<222> LOCATION: (18)..(18)
<223> OTHER INFORMATION: AMIDATION

<400> SEQUENCE: 15

Lys Ser Gly Lys Arg Glu Leu Asp Trp Ser Trp Ala Gln Lys Asn Lys
1               5                   10                  15

Thr Ile
```

STAPLED PEPTIDES AND USES THEREOF

CROSS-REFERENCE TO RELATED APPLICATIONS

This application is a U.S. National Stage Application pursuant to 35 U.S.C. § 371 of International Patent Application PCT/EP2017/084309, filed on Dec. 22, 2017, and published as WO 2018/115400 on Jun. 28, 2018, which claims priority to European Patent Application 16306788.7, filed on Dec. 22, 2016, all of which are incorporated herein by reference in their entireties for all purposes.

DOMAIN OF THE INVENTION

The present invention provides new peptidomimetic macrocycles also named stapled peptides, derived from IRAK2 and IRAKM (also called IRAK3) protein-binding region of IRAK4, and uses thereof, in particular their use as inhibitors of inflammatory pathways. The term "IRAK" as used herein refers to Interleukin-Receptor Associated Kinase, which becomes associated with an interleukin receptor (IL-R) upon stimulation. IRAK genes are partially responsible for interleukin-induced upregulation of the transcription factor NF-kappa B.

BACKGROUND OF THE INVENTION

Signal transduction by the Toll-like receptors (TLRs) is central to host defense against many pathogenic microorganisms and also underlies a large burden of human diseases, including chronic inflammatory disorders.

Inflammatory disorders and autoimmune diseases are important public health problems that affect the life of millions of people worldwide and require specific therapeutic interventions. The TLR signaling pathway has been studied in infectious and inflammatory disorders, as well as cancer. Targeting this signaling pathway may be relevant in autoimmune diseases such as rheumatoid arthritis, multiple sclerosis and Crohn's disease, as well as other common diseases that are associated with the deregulation of inflammatory signals, such as type 2 diabetes, infections, sepsis, cancer and cardiovascular diseases.

Thus, the mechanism and regulation of signaling by TLRs is of considerable interest for the development of novel and specific anti-inflammatory therapies (O'Neill et al. Nat. Rev. Immunol. 2007).

TLRs activation induces a cascade of downstream signal transducer interactions that promote the assembly of a multiproteic complex, namely the 'Myddosome' complex, activate the nuclear factor-kB (NF-kB), and lead to the production of pro-inflammatory cytokines (TNFα, IL-1β, IL-6 . . . ). The Myddosome is an oligomeric structure containing several molecules of MYD88, IRAK4 and IRAK2. (Lin et al. Nature 2010).

Currently big pharmaceutical groups are working on the inhibition of IRAK4 kinase activity. Some compounds are in pre-clinical phase (Chaudhary et al, Journal of Medicinal Chemistry, 2015).

However, although blocking the production of proinflammatory cytokines is well admitted as a therapeutic goal, there are no currently drugs on the market inhibiting this pathway by a strategy that blocks the production of proinflammatory cytokines (IL1 beta, TNF alpha and IL6) upstream their secretion. In addition, IRAK2 and IRAKM are pseudo-kinases, and their activity cannot thus be inhibited through regular kinase inhibitor strategies. Zhou and coworkers (Hao Zhou et al., The EMBO Journal (2013) 32, 583-596) demonstrated that IRAKM interacts with Myd88-IRAK4, as IRAK2.

So there is a need of new compounds that can inhibit the signaling TLR pathway of the production of cytokines TNFα, IL-6 and IL1β.

The inventors designed specific macrocycle peptides, also named stapled peptides, which inhibit the IRAK2/IRAK4 interactio The originality of this invention is to treat inflammatory and infectious diseases soon as they occur in the body, acting at a new target, which is not currently proposed. Indeed, the only effective anti-TNFα treatments available today are monoclonal antibodies such as adalimumab, infliximab or etanercept. However, antibodies are heavy processing and do not allow to block the upstream inflammatory pathways.

Inhibiting the interaction of IRAK-2 with IRAK-4 through the stapled peptides is therefore a strategic alternative choice.

SUMMARY OF THE INVENTION

The present invention relates to specific peptidomimetic macrocycles derived from IRAK2 and IRAKM and protein-binding region of IRAK4 that inhibit the inflammation pathway activated through TLR and IL1R. The invention further relates to their method of preparation, pharmaceutical composition containing these peptidomimetic macrocycles, and their uses, alone or in combination with an additional compound chosen from anti-inflammatory or cellular targeting compounds, for use in the prevention or the treatment of inflammation, in particular acute or chronic inflammatory disorders.

Definitions According to the Invention

The term "peptidomimetic macrocycle" or "crosslinked polypeptide" or "stapled peptide" according to the invention refers to a compound comprising a plurality of amino acid residues joined by a plurality of peptide bonds and at least one macrocycle-forming linker which forms a macrocycle between a first naturally-occurring or non-naturally occurring amino acid residue (or analog) and a second naturally-occurring or non-naturally-occurring amino acid residue (or analog) within the same molecule.

Peptidomimetic macrocycles include embodiments where the macrocycle-forming linker connects the a-carbon of the first amino acid residue (or analog) to the a-carbon of the second amino acid residue (or analog).

A "corresponding uncrosslinked polypeptide" or "linear peptide" when referred to in the context of a peptidomimetic macrocycle is understood to relate to a polypeptide of the same length as the macrocycle and comprising the equivalent natural amino acids of the wild-type sequence corresponding to the macrocycle.

The terms "peptide" or "polypeptide" according to the invention encompasses two or more naturally or non-naturally-occurring amino acids joined by a covalent bond (e.g., an amide bond). Peptides according to the invention generally have a length comprised between 8 to 30 amino acids.

The term "amino acid" according to the invention refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes without limitation, a-amino acids, natural amino acids, non-natural amino acids, and amino acid analogs.

The term "naturally occurring amino acid" according to the invention refers to any one of the twenty L-amino acids commonly found in peptides synthesized in nature, namely the L-isomers of alanine (Ala or A), Arginine (Arg or R), asparagine (Asn or N), aspartic acid (Asp or D), cysteine (Cys or C), glutamic acid (Glu or E), glutamine (Glu or Q), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). In case of naturally occurring amino acids which are sensitive to oxidation, the amino acid in the peptidomimetic is replaced with a conservative amino acid substitution; for example methionine (M) is replaced by norleucine (Nle), without impacting its biological activity.

The term "amino acid analog" or "non-natural amino acid" according to the invention refers to a molecule which is structurally similar to an amino acid and which can be substituted for an amino acid in the formation of a peptidomimetic macrocycle. As an example, ornithine is an analog of lysine.

Amino acid analogs include, without limitation, compounds which are structurally identical to an amino acid, as defined herein, except for the inclusion of one or more additional methylene groups between the amino and carboxyl group (e.g., α-amino β-carboxy acids), or for the substitution of the amino or carboxy group by a similarly reactive group (e.g., substitution of the primary amine with a secondary or tertiary amine, or substitution of the carboxy group with an ester).

The term "non-natural amino acid" according to the invention refers to an amino acid which is not one of the twenty amino acids commonly found in peptides synthesized in nature, but instead is generated through chemical synthesis or through chemical modification of a naturally occurring amino acid.

The term "non-essential" amino acid residue according to the invention is a residue that can be altered from the wild-type sequence of a polypeptide without abolishing or substantially abolishing its essential biological or biochemical activity (e.g., receptor binding or activation). The term "essential" amino acid residue according to the invention is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "biological activity" encompasses structural and functional properties of a macrocycle of the invention. Biological activity is, e.g., structural stability, alpha-helicity, affinity for a target, resistance to proteolytic degradation, cell penetrability, intracellular stability, in vivo stability, or any combination thereof.

The terms "i,", "i+3", "i+4," and "i+7" according to the invention refer to the positions of the amino acids within the peptide that become covalently bonded to one another upon formation of the staple. The "i" position refers to the position of the amino acid that is nearest to the amino terminus of the peptide. The "i+3" position is 3 amino acids downstream (3 amino acids further towards the carboxy-terminus) of the "i" position, the "i+4" position is 4 amino acids downstream (4 amino acids further towards the carboxy-terminus) of the "i" position, and the "i+7" position is 7 amino acids downstream of the "i" position. Upon formation of the staple, a covalent bond is formed between the amino acid at position i and the amino acid at position i+3, i+4 or i+7.

The term "helical stability" according to the invention refers to the maintenance of a helical structure by a peptidomimetic macrocycle provided herein as measured by circular dichroism.

The term "alkylene" refers to a divalent alkyl (i.e. —R—).

The term "alkenyl" refers to a hydrocarbon chain that is a straight chain or branched chain having one or more carbon-carbon double bonds. The alkenyl moiety contains the indicated number of carbon atoms. For example, C2-C10 indicates that the group has from 2-10 (inclusive) carbon atoms in it.

The term "alkynyl" refers to a hydrocarbon chain that is a straight chain or branched chain having one or more carbon-carbon triple bonds.

DETAILED DISCLOSURE OF THE INVENTION

Peptidomimetic Macrocycles (Stapled Peptides)

Stapled peptides according to the invention include a covalent bond between the side chains of two amino acids in the peptide. Peptide stapling can be used to physically constrain a peptide into a specific conformation (e.g., to physically constrain a peptide into its native α-helical state). This can in turn enhance the pharmacological properties of a peptide by helping to retain the native structure needed to interact with a target molecule, increasing cell penetration, and/or protecting the peptide from proteolytic degradation.

The design of the stapled peptides according to the invention is based on the inhibition of the interaction of Myd88/IRAK4/IRAK2 complex. This protein complex, once formed, induces the synthesis of several pro-inflammatory cytokines, including IL-1β, TNFα and IL-6, through the activation of the NF-kB pathway (FIG. 1). A crystallographic study and Ala-scan virtual screening of the Myd88/IRAK4/IRAK2 complex revealed the presence of an α-helix in IRAK2, which we named IRAK2 54-71, interacting with IRAK4 surface. This interaction between IRAK4 and IRAK2 is essential for the activity of the Myd88/IRAK4/IRAK2 complex. The strategy adopted was to develop stapled peptides of this sequence, in order to mimic the IRAK2 α-helix and see whether these peptides could replace IRAK2 protein within the complex, thereby inhibiting its formation and the downstream production of pro-inflammatory cytokines.

A closer study of the literature (Du et al. Cell Commun Signal. 2014) showed that IRAKM (IRAK3) protein is a natural protein that inhibits the complex Myd88/IRAK4/IRAK2 by replacing IRAK2. The lack of crystallographic data on IRAKM has led us to perform sequence alignments between IRAK2 and IRAKM in order to see whether this protein has identical amino acids to those of the α-helix of IRAK2 54-71. This study showed that 50% of the amino acids are conserved within this α-helix. So we also synthesized stapled peptides of IRAKM, which we named IRAKM 66-83.

The sequences are defined hereunder:

```
IRAK2 54-71:
                              (SEQ ID NO 1)
VSITRELLWWWGMRQATV

IRAKM 66-83:
                              (SEQ ID NO 2)
KSGTRELLWSWAQKNKTI
```

The amino-acids in the positions 5-6, 9-11, 13-15 preferably 14-15 of the IRAK2 54-71 (SEQ ID No1) and respectively the amino acids in the positions 5-6, 9-11, 13-15 preferably 13-14 of the IRAKM 66-83 (SEQ ID No2) are essential, which means that a modification of the said amino-acids will impact their functionality or activity and structure in α-helix. As a consequence, the designed stapled peptides according to the invention were prepared taken into account the criticity of the amino-acids positions.

After establishing the synthetic strategy and the stapling positions, several peptides were synthesized. Among them, we selected six peptides to describe their activity: two similar linear sequences of the α-helix of IRAK2 and IRAKM, and four stapled peptides derived from these sequences. An additional peptide was synthesized to have a negative control stapled peptide in biological tests. This peptide, which we named Mock S, a random stapled peptide that does not correspond to sequences of IRAK2 54-71 (SEQ ID No1) and IRAKM 66-83 (SEQ ID No2).

The sequences were listed in the following table 1.

TABLE 1

| NO SEQ | NAME | SEQUENCE | TYPE |
|---|---|---|---|
| SEQ ID NO 1 | IRAK2 54-71 | VSITRELLW WWGMRQATV | Linear peptide |
| SEQ ID NO 2 | IRAKM 66-83 | KSGTRELLW SWAQKNKTI | Linear peptide |
| SEQ ID NO 3 | IRAK2 S1 JMV6645 | Ac-$S_5$-REL-$S_5$- WWWGBRQA-$NH_2$ | Stapled peptide |
| SEQ ID NO 4 | IRAK2 S2 JMV6646 | Ac-RREL-$S_5$-WWW- $S_5$-BRQA-$NH_2$ | Stapled peptide |

TABLE 1-continued

| NO SEQ | NAME | SEQUENCE | TYPE |
|---|---|---|---|
| SEQ ID NO 5 | IRAKM S1 JMV6647 | Ac-KSG-$S_5$-REL- $S_5$-WSWAQK-$NH_2$ | Stapled peptide |
| SEQ ID NO 6 | IRAKM S2 JMV6648 | Ac-RREL-$S_5$-WSW- $S_5$-QK-$NH_2$ | Stapled peptide |
| SEQ ID NO 7 | IRAK2 Li | Ac-RRELLWWW GBRQA-$NH_2$ | Linear peptide |
| SEQ ID NO 8 | IRAKM Li | Ac-RRELLWSW AQK-$NH_2$ | Linear peptide |
| SEQ ID NO 9 | Mock-S | Ac-ITF-$S_5$-NLL- $S_5$-YYGP-$NH_2$ | Stapled peptide (control) |
| SEQ ID NO 10 | IRAK2- JMV6650 | Ac-VSI-$S_5$-REL- $S_5$-WWWGBRQATV-$NH_2$ | Stapled peptide |
| SEQ ID NO 11 | IRAKM- JMV6649 | Ac-KSG-$S_5$-REL-$S_5$- WSWAQKNKTI-$NH_2$ | Stapled peptide |
| SEQ ID NO 12 | IRAK2 JMV6651 | Ac-K-REL-D-WWW GBRQA-$NH_2$ | Stapled peptide |
| SEQ ID NO 13 | IRAK2 JMV6652 | Ac-VSI-K-REL-D- WWWGBRQATV-$NH_2$ | Stapled peptide |
| SEQ ID NO 14 | IRAKM JMV6653 | Ac-KSG-K-REL-D- WSWAQK-$NH_2$ | Stapled peptide |
| SEQ ID NO 15 | IRAKM JMV6654 | Ac-KSG-K-REL-D- WSWAQKNKTI-$NH_2$ | Stapled peptide |

The methionine 'M' in position 13, which is sensitive to oxidation, has been replaced by a norleucine 'B', which is a conservative amino acid substitution.

In an alternative embodiment for the SEQ No12 to SEQ ID No15, the lysine (K) may be replaced by ornithine and/or the aspartic acid (D) may be replaced by glutamic acid (E).

IRAK2 S1 is also named IRAK2-JMV6645 in the present invention.

IRAK2 S2 is also named IRAK2-JMV6646 in the present invention.

IRAKM S1 is also named IRAKM-JMV6647 in the present invention.

IRAKM S2 is also named IRAKM-JMV6648 in the present invention.

Amino acids represented as "S5" are alpha-Me S5-pentenyl-alanine olefin amino acids connected by an all-carbon i to i+4 crosslinker comprising one double bond.

"Ac" represents acetyl.

"B" represents the amino acid Norleucin.

These staple peptides are also represented in the following Table 2a and Table 2b:

TABLE 2a

SEQ ID NO 3   IRAK2 S1
              JMV6645

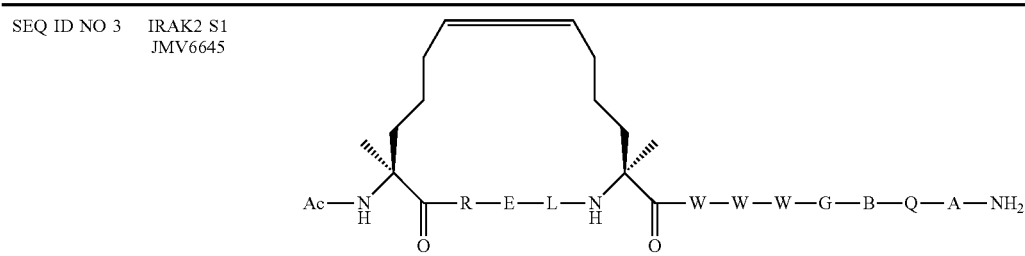

TABLE 2a-continued
| SEQ ID NO 4 | IRAK2 S2 JMV6646 | 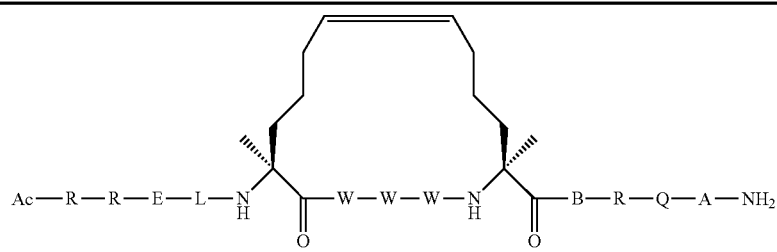 |
| SEQ ID NO 5 | IRAKM S1 JMV6647 | 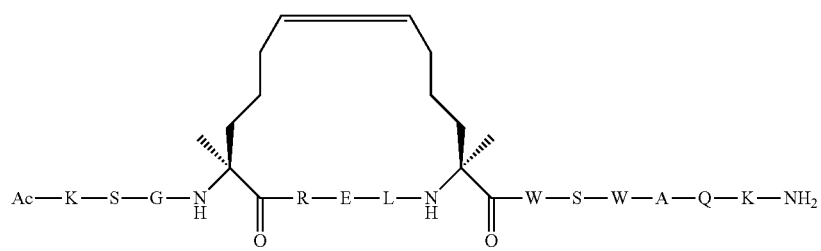 |
| SEQ ID NO 6 | IRAKM S2 JMV6648 | 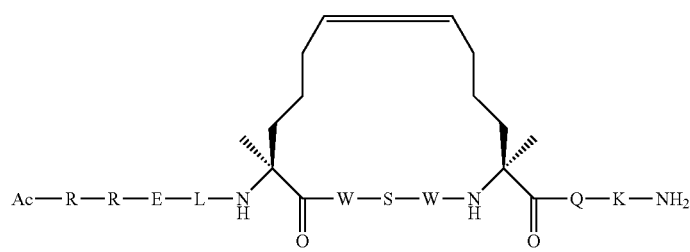 |
TABLE 2b
| NO SEQ | NAME | |
| --- | --- | --- |
| SEQ ID NO 3 | IRAK2 S1 JMV6645 | 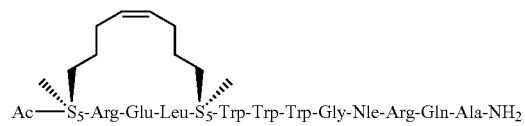 |
| SEQ ID NO 4 | IRAK2 S2 JMV6646 | 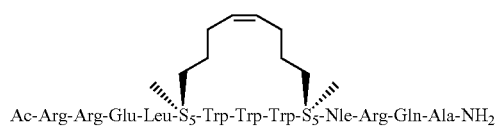 |
| SEQ ID NO 5 | IRAKM S1 JMV6647 | 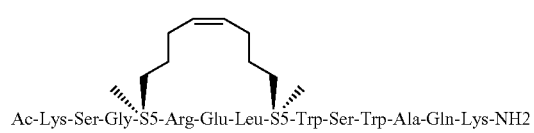 |
| SEQ ID NO 6 | IRAKM S2 JMV6648 | 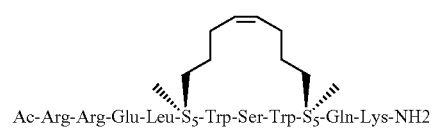 |
| SEQ ID NO 10 | IRAK2 JMV6650 | 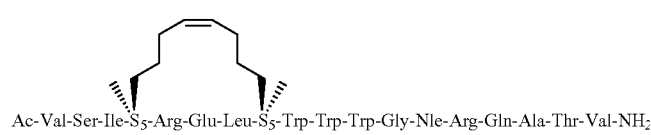 |

TABLE 2b-continued

| NO SEQ | NAME | | |
|---|---|---|---|
| SEQ ID NO 11 | IRAKM JMV6649 |  Ac-Lys-Ser-Gly-S$_5$-Arg-Glu-Leu-S$_5$-Trp-Ser-Trp-Ala-Gln-Lys-Asn-Lys-Thr-Ile-NH$_2$ | |
| SEQ ID NO 12 | IRAK2 JMV6651 | 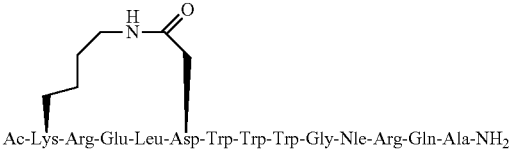 Ac-Lys-Arg-Glu-Leu-Asp-Trp-Trp-Trp-Gly-Nle-Arg-Gln-Ala-NH$_2$ | |
| SEQ ID NO 13 | IRAK2 JMV6652 | 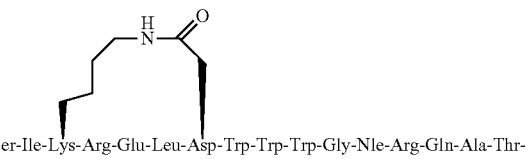 Ac-Val-Ser-Ile-Lys-Arg-Glu-Leu-Asp-Trp-Trp-Trp-Gly-Nle-Arg-Gln-Ala-Thr-Val-NH$_2$ | |
| SEQ ID NO 14 | IRAKM JMV6653 | 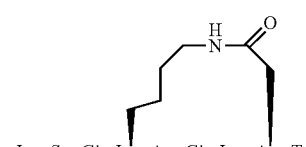 Ac-Lys-Ser-Gly-Lys-Arg-Glu-Leu-Asp-Trp-Ser-Trp-Ala-Gln-Lys-NH2 | |
| SEQ ID NO 15 | IRAKM JMV6654 | 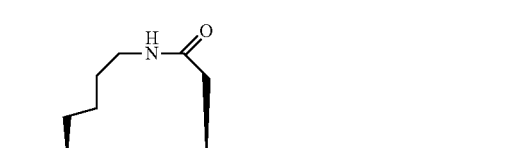 Ac-Lys-Ser-Gly-Lys-Arg-Glu-Leu-Asp-Trp-Ser-Trp-Ala-Gln-Lys-Asn-Lys-Thr-Ile-NH$_2$ | |

Covalent side-chain to side-chain linkage ("stapling") within small α-helical segments derived from a protein overcome the little or no helical character shown in solution by these oligopeptides when they are excised from their native context. Thus, incorporation of short hydrocarbon chains as «staples» has been shown to enhance helicity, resistance to proteolysis and cell permeability (Lau et al., Chem. Soc. Rev. 2015, 44, 91-102; Walensky and Bird, J. Med. Chem., 2014, 57, 6275-6288; Guerlavais and Sawyer, Annual reports in Med. Chem., 2014, 49, 331-345). Then the peptidomimetic macrocycles possess improved pharmaceutical properties relative to their corresponding uncross-linked (e.g, linear) peptidomimetic macrocycles or stapled peptides. These improved properties include improved bio-availability and in vivo stability (resistance to hydrolysis).

When stapled peptides are used to physically constrain a peptide into its native α-helical state as it is the case according to the invention, it is desirable to form the staple between the i and i+3 positions of a peptide or the i and i+4 positions of a peptide or between the i and i+7 positions of a peptide. This because upon formation of the alpha helix, the amino acid side chains of the amino acids at the i, i+3, the i, i+4, and i+7 positions will be located on the same face of the helix.

Examples of stapled peptides with staple between i and i+3, i and i+4, and i and i+7 positions are represented in FIG. 2A.

A first object of the invention is a peptidomimetic macrocycle comprising at least one macrocycle-forming linker and an amino acid sequence chosen from the group consisting of:

(i) an amino acid sequence with at least about 50%, 60%, 70%, 80%, 90%, or 95% sequence identity to a human sequence IRAK2 54-71 (SEQ ID No1) and 100% identity with the amino acids in the positions 5-6, 9-11, 13-15 preferably 14-15 or (ii) an amino acid sequence with at least about 50%, 60%, 70, 80%, 90%, or 95% sequence identity to a human sequence IRAKM 66-83 (SEQ ID No2) and 100% identity with the amino acids in the positions 5-6, 9-11, 13-15 preferably 13-14, wherein the peptidomimetic macrocycle comprises an α-helix and at least two natural or non-natural amino acids crosslinked by a macrocycle-forming linker.

In a particular embodiment, the peptidomimetic macrocycle comprises at least one macrocycle-forming linker and an amino acid sequence chosen from the group consisting of:

(i) an amino acid sequence with at least about 50%, 60%, 70%, 80%, 90%, or 95% sequence identity to a human sequence IRAK2 54-71 (SEQ ID No1) and 100% identity with the amino acids in the positions 5-7, 9-11, 14-15 or (ii) an amino acid sequence with at least about 50%, 60%, 70, 80%, 90%, or 95% sequence identity to a human sequence IRAKM 66-83 (SEQ ID No2) and 100% identity with the amino acids in the positions 5-7, 9-11, 13-14, wherein the peptidomimetic macrocycle comprises an α-helix and at least two natural or non-natural amino acids crosslinked by a macrocycle-forming linker.

The sequence identity is calculated by sequence alignment according to known methods in the art.

To determine the percent identity of two amino acids sequences, the sequences are aligned for optimal comparison. For example, gaps can be introduced in the sequence of a first amino acid sequence for optimal alignment with the second amino acid sequence. The amino acid residues at corresponding amino acid positions are then compared. When a position in the first sequence is occupied by the same amino acid residue as the corresponding position in the second sequence, the molecules are identical at that position. The percent identity between the two sequences is a function of the number of identical positions shared by the sequences. Hence % identity=number of identical positions/total number of overlapping positions ×100.

In this comparison the sequences can be the same length or can be different in length. Optimal alignment of sequences for determining a comparison window may be conducted by the local homology algorithm of Smith and Waterman (J. Theor. Biol., 1981), by the homology alignment algorithm of Needleman and Wunsch (J. Mol. Biol, 1972), by the search for similarity via the method of Pearson and Lipman (Proc. Natl. Acad. Sci. U.S.A., 1988), by computerized implementations of these algorithms (GAP, BEST-FIT, FASTA and TFASTA in the Wisconsin Genetics Software Package Release 7.0, Genetic Computer Group, 575, Science Drive, Madison, Wis.) or for instance using publicly available computer software such as BLAST[2]. When using such software, the default parameters, e.g for gap penalty or extension penalty, are preferably used. The best alignment (i.e. resulting in the highest percentage of identity over the comparison window) generated by the various methods is selected.

In a particular embodiment, the peptidomimetic macrocycle comprises at least one macrocycle-forming linker and an amino acid sequence having at least 70% sequence identity to a human sequence IRAK2 54-71 (SEQ ID No1) and 100% identity with the amino acids in the positions 5-6, 9-11, 14-15 or to a human sequence IRAKM 66-83 (SEQ ID No2) and 100% identity with the amino acids in the positions 5-6, 9-11, 13-15 preferably 13-14.

The positions of the amino acids are determined according to the referred sequence SEQ ID.

In another particular embodiment, the peptidomimetic macrocycle comprises at least one macrocycle-forming linker and an amino acid sequence having at least 80% sequence identity to a human sequence IRAK2 54-71 (SEQ ID No1) and 100% identity with the amino acids in the positions 5-6, 9-11, 14-15 or to a human sequence IRAKM 66-83 (SEQ ID No2) and 100% identity with the amino acids in the positions 5-6, 9-11, 13-15 preferably 13-14.

In another particular embodiment, the peptidomimetic macrocycle comprises at least one macrocycle-forming linker and an amino acid sequence having at least 90% sequence identity to a human sequence IRAK2 54-71 (SEQ ID No1) or to a human sequence IRAKM 66-83 (SEQ ID No2) and 100% identity with the amino acids in the positions 5-6, 9-11, 13-15. In a particular and preferred embodiment, the peptidomimetic macrocycle comprises at least one macrocycle-forming linker and an amino acid sequence having between 65% and 90% sequence identity to a human sequence IRAK2 54-71 (SEQ ID No1) and 100% identity with the amino acids in the positions 5-6, 9-11, 14-15, or to a human sequence IRAKM 66-83 (SEQ ID No2) and 100% identity with the amino acids in the positions 5-6, 9-11, 13-14.

In a particular and preferred embodiment, the peptidomimetic macrocycle comprises at least one macrocycle-forming linker and an amino acid sequence having between 68% and 90% sequence identity to a human sequence IRAK2 54-71 (SEQ ID No1) and 100% identity with the amino acids in the positions 5-6, 9-11, 14-15.

In a particular and preferred embodiment, the peptidomimetic macrocycle comprises at least one macrocycle-forming linker and an amino acid sequence having between 70% and 90% sequence identity to a human sequence IRAKM 66-83 (SEQ ID No2) and 100% identity with the amino acids in the positions 5-6, 9-11, 13-14.

The amino acids in the positions 5-6, 9-11, 13-15 preferably 14-15 of IRAK2 54-71 (SEQ ID No1) and respectively the amino acids in the positions 5-6, 9-11, 13-14 of IRAKM 66-83 (SEQ ID No2) are essential amino acids for biological activity of the peptidomimetic macrocycle as defined above.

The amino acids in the positions 5-7, 9-11, 14-15 of IRAK2 54-71 (SEQ ID No1) and respectively the amino acids in the positions 5-7, 9-11, 13-14 of IRAKM 66-83 (SEQ ID No2) may also be considered as essential amino acids for biological activity of the peptidomimetic macrocycle as defined above.

Several types of peptide staples or macrocycle linkers may be mentioned: (a) a lactam bridge, (b) a hydrocarbon bridge, (c) a metal-ion clip; (d) a hydrogen bond surrogate; and (e) a heterocycle bridge. Any of these types of staples, or other peptide staples known in the art, can be used in connection with any of the peptides described herein.

Lactam bridges can be formed glutamic acid or aspartic acid and lysine (or its analog ornithine) residues of a peptide. The glutamic acid or aspartic acid and lysine residues may be present in the native sequence of the peptide. Alternatively, amino acid substitutions for glutamic acid, aspartic acid and/or lysine (or its analog ornithine) at the desired positions of the peptide or may be introduced at the desired positions during peptide synthesis. In a particular embodiment, lactam bridges are formed using the lysine and aspartic acid residues.

In a particular embodiment, the one or more substitutions can comprise substitutions with lysine derivative residue at position i and a substitution with aspartic derivative at position i+3 or position i+4 or position i+7, preferably position i+4.

Hydrocarbon bridges (e.g., olefin bridges) can be formed between two allylglycine residues in a peptide. Two allylglycine residues can be introduced into a peptide at the desired positions, and then the hydrocarbon bridge can be formed using standard methods known in the art. When allylglycine residues are used for formation of hydrocarbon bridges, the substitutions are preferably made at the i and i+4 positions of the peptide.

In another particular embodiment, hydrocarbon bridges can also be formed using the alanine derivatives S5, R8, and/or R5, e.g "S5-olefin amino acid" is (S)-a-(2'-pentenyl) alanine, the "R8 olefin amino acid" is (R)-a-(2'-octenyl) alanine and "R5-olefin amino acid" is (R)-a-(2'-pentenyl) alanine.

In a particular embodiment, the one or more substitutions can comprise substitutions with alanine derivative R5 residues at position i and a substitution with alanine derivative S5 at position i+3.

In another embodiment, the one or more substitutions can comprise a substitution with alanine derivative R8 at position i and a substitution with alanine derivative S5 at one of positions i+4 and i+7.

In a metal-ion clip, a bridge is formed through coordinate bonds to a metal-ion (e.g., a rhenium, ruthenium, or palladium ion).

In a hydrogen bond surrogate, a hydrocarbon bridge is formed between the amino-terminal nitrogen atom of a peptide to an amino acid side chain.

In a particular embodiment of the invention, lactam bridge or hydrocarbon bridge are used as macrocycle linker.

In a preferred embodiment of the invention, the macrocycle-forming linker comprises a hydrocarbon chain, saturated or unsaturated, and optionally substituted.

The hydrocarbon chain may contain from 6 to 20 carbon atoms, preferably from 6 to 14 carbon atoms.

In a particular embodiment, a —$CH_2$— group of the hydrocarbon chain as defined above has been replaced with an amide function —NH—CO—.

In a preferred embodiment, the hydrocarbon chain is unsaturated, which means that it contains a double bond.

In a particular embodiment, the hydrocarbon chain may be substituted. In particular, dihydroxy compounds may be made from the double chain and these dihydroxy compounds may be substituted.

In a particular embodiment, the macrocycle-forming linker comprises a hydrocarbon chain chosen from the group consisting of alkylene, alkenylene, alkynylene, and derived thereof, preferably alkylene.

In a particular embodiment, the macrocycle-forming linker comprises a saturated or unsaturated, notably saturated hydrocarbon chain in which a —$CH_2$— group has been replaced with an amide function —NH—CO—.

In a particular embodiment, the macrocycle linker is a lactam bridge, which consists in a hydrocarbon chain as defined above in which a —$CH_2$— group has been replaced with an amide function —NH—CO—.

In some embodiments, the at least one macrocycle-forming linker is a straight chain alkenyl with 6 to 14 carbon atoms. In some embodiments, the at least one macrocycle-forming linker is a straight chain alkenyl with 8 to 12 carbon atoms, for example 8, 9, 10, 11 or 12 carbon atoms.

In a particular embodiment, the two natural or non-natural amino acids crosslinked by a macrocycle-forming linker are spaced by at least three amino acids (i and i+3), four amino acids (i and i+4), or seven aminoacids (i and i+7), preferably four amino acids (i and i+4). It is preferably said that the two natural or non-natural amino acids crosslinked by a macrocycle-forming linker are at i and i+3 positions, or i and i+4 positions, or i and i+7 positions, preferably at i and i+4 positions.

In a particular embodiment, the macrocycle-forming linker connects amino acids at positions 4 (i) and 8 (i+4) of the sequence IRAK2 54-71 (SEQ ID No1). In another particular embodiment, the macrocycle-forming linker connects amino acids at positions 4 (i) and 8 (i+4) of the sequence IRAKM 66-83 (SEQ ID No2).

In another particular embodiment, the macrocycle-forming linker connects amino acids at positions 8 (i) and 12 (i+4) of the sequence IRAK2 54-71 (SEQ ID No1). In another particular embodiment, the macrocycle-forming linker connects amino acids at positions 8 (i) and 12 (i+4) of the sequence IRAKM 66-83 (SEQ ID No2).

Stapled peptides sequences and amino acids positions are represented in FIG. 2B.

In a particular embodiment, a peptidomimetic macrocycle according to the invention comprises at least two pairs of natural or non-natural amino acids crosslinked each and independently by one macrocycle-forming linker.

For example, the peptide can comprise one or more first substitutions at a first position i, a first position i+3, a first position i+4, and/or a first position i+7, wherein the one or more first substitutions allows for the formation of a covalent bond between the amino acid at first position i and the amino acid at first position i+3, first position i+4 or first position i+7; and one or more second substitutions at a second position i, a second position i+3, a second position i+4, and/or a second position i+7, wherein the one or more second substitutions allows for the formation of a covalent bond between the amino acid at second position i and the amino acid at a second position i+3, second position i+4 or second position i+7.

In such embodiments, the at least one macrocycle-forming linker comprises a first and a second macrocycle-forming linker, wherein the first macrocycle-forming linker connects a first and a second amino acid, wherein the second macrocycle-forming linker connects a third and a fourth amino acid, wherein the first amino acid is upstream of the second amino acid, the second amino acid is upstream of the third amino acid, and the third amino acid is upstream of the fourth amino acid. The at least one macrocycle-forming linker may comprise a first and a second macrocycle-forming linker that are separated by 2, 3, 4, 5, 6, or 7 amino acids. In some embodiments, the at least one macrocycle-forming linker comprises a first and a second macrocycle-forming linker that are separated by 4 or 5 amino acids.

In a preferred embodiment, a peptidomimetic macrocycle according to the invention comprises an amino acid sequence chosen from the group consisting of SEQ ID No 3 (IRAK2 S1-JMV6645): Ac-X-REL-X-WWWGBRQA-$NH_2$ SEQ ID No 4 (IRAK2 S2-JMV6646): Ac-RREL-X-WWW-X-BRQA-$NH_2$ SEQ ID No5 (IRAKM S1-JMV6647): Ac-KSG-X-REL-X-WSWAQK-$NH_2$ SEQ ID No6 (IRAKM S2-JMV6648): Ac-RREL-X-WSW-X-QK-$NH_2$ SEQ ID No10 (IRAK2-JM6650): Ac-VSI-X-REL-X-WWWGBRQA-$NH_2$ SEQ ID No11 (IRAKM-JM6649): Ac-KSG-X-REL-X-WSWAQKNKTI-$NH_2$ wherein non-natural amino acids X are terminated by olefins and crosslinked by a macrocycle-forming linker, or

```
SEQ ID NO 12 (IRAK2-JMV6651):
Ac-K-REL-D-WWWGBRQA-NH₂

SEQ ID NO 13 (I RAK2-JMV6652):
Ac-VSI-K-REL-D-WWWGBRQATV-NH₂

SEQ ID NO 14 (IRAKM-JMV6653):
Ac-KSG-K-REL-D-WSWAQK-NH₂

SEQ ID NO 15 (IRAKM-JMV6654):
Ac-KSG-K-REL-D-WSWAQKNKTI-NH₂
``` wherein natural amino acids Lysine (K) and Aspartic acid (D) and crosslinked by a macrocycle-forming linker.

In an alternative embodiment for SEQ ID No12 to SEQ ID No15, lysine (K) may be replaced by ornithine and/or aspartic acid (D) may be replaced by glutamic acid (E).

In a preferred embodiment, the non-natural amino acid X is (S)-2(4-pentenyl)alanine (represented by S5) or a derived thereof.

In another preferred embodiment, the natural amino acids crosslinked by a macrocycle-forming linker are lysine and aspartic acid residues.

The following preferred configurations can be used to create hydrocarbon bridges in peptides using the alanine derivatives S5, R8, and/or R5:

in a first embodiment, the one or more substitutions can comprise substitutions with alanine derivative S5 residues at positions i and i+4;

in another embodiment, the one or more substitutions can comprise a substitution with alanine derivative R8 at position i and a substitution with alanine derivative S5 at position i+7;

in another embodiment, the one or more substitutions can comprise substitutions with alanine derivative R5 residues at position i and a substitution with alanine derivative S5 at position i+3.

Such configurations are represented in FIG. 2A.

The amino acid at position i is preferably covalently bonded to the amino acid at position i+3, i+4 or i+7.

In a preferred embodiment, the one or more substitutions comprise substitutions with alanine derivative S5 residues at positions i and i+4.

In particular embodiment, the non-natural amino acids alpha-Me S5-pentenyl-alanine olefin amino acids (S5) are connected by an all-carbon i to i+4 crosslinker comprising one double bond.

The peptidomimetic macrocycle according to the invention generally comprises from 8 to 30 amino acids, preferably from 10 to 20 amino acids.

The stapled peptides according to the invention can also encompass functionally equivalent variants or analogues of the peptides of the present invention. This includes peptides having peptides having one or more conservative or non-conservative amino acid substitutions as compared to the sequences of the peptides described herein. The substitution is preferably a conservative substitution, and does not negatively impact the biological or structural properties of the peptide. Amino acid substitutions may be generally based on the relative similarity of the amino acid side-chain substituents, for example, their hydrophobicity, hydrophilicity, charge, size and the like. Thus, conservative amino acid changes means an amino acid change at a particular position which may be of the same type as originally present; i.e. a hydrophobic amino acid exchanged for a hydrophobic amino acid, a basic amino acid for a basic amino acid, etc. Examples of conservative substitutions may include, without limitation, the substitution of non-polar (hydrophobic) residues such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another, the substitution of a branched chain amino acid, such as isoleucine, leucine, or valine for another, the substitution of one aromatic amino acid, such as phenylalanine, tyrosine or tryptophan for another.

Examples of such conservative changes are well known to the skilled artisan and are within the scope of the present invention. Conservative substitution may also include the use of a chemically derivatized residue in place of a non-derivatized residue provided that the resulting peptide is a biologically functional equivalent to the peptides of the invention.

Any of stapled peptides described herein can also include various chemical modifications. For example, any of the peptides can be amidated at its carboxy-terminus. Alternatively or in addition, any of the peptides can be acetylated at its amino-terminus. These modifications reduce the overall charge of a peptide, which can increase stability because the terminal acetylation/amidation generates a closer mimic of the native protein. Therefore, these modifications can increase the biological activity of a peptide. Other modifications can also be made to any of the peptides described herein. For example, the peptide can be phosphorylated, glycosylated, PEGylated, lipidated, functionalized with a cellulose or a modified cellulose, or a combination thereof.

In a particular and preferred embodiment, the stapled peptides of the invention are designed from sequences closer to the native sequences in order to obtain a better recognizing of the target and an improved inhibitory efficiency.

Any of the peptides described herein can further comprise a detectable label. The detectable label can biotin, a magnetic label, a paramagnetic label, a radioactive label, a fluorescent label, a radiodense label, an enzyme, and a combination thereof.

In a preferred embodiment, a peptidomimetic macrocycle according to the invention comprises additionally at least one spacer.

The spacer may be present between the stapled peptide and the additional peptide for improving its cell targeting or penetration.

As 'additional peptide for improving cell targeting or penetration of the stapled peptide', mention may be made of cell-penetrating peptide such as Tat, Penetratin or Pep1.

In a particular embodiment, a peptidomimetic macrocycle according to the invention comprises additionally at least one cell-penetrating peptide.

Method of Preparation of Peptidomimetic Macrocycles

Various methods to effect formation of peptidomimetic macrocycles are known in the art. For example, the preparation of peptidomimetic macrocycles according to the invention is described in Yu et al. (Chem. Soc. Rev., 2015, 44, 91).

Peptide synthesis may be performed manually, using solid phase conditions, AmphiSpheres rink amide (Agilent), and Fmoc main-chain protecting group chemistry. For the coupling of natural Fmoc-protected amino acids (Iris biotech), non-natural amino acids S5, R5 and R8 or natural amino acids Lys (K) and Asp (D), equivalents of amino acid and specific molar ratio of coupling reagents were employed. The N-termini of the synthetic peptides were acetylated, while the C-termini were aminated.

One preferred manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Following incorporation of non-natural amino acids S5, R5 and R8, into precursor polypeptides, the terminal olefins are reacted with a metathesis catalyst, leading to the formation of the peptidomimetic macrocycle.

In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. Various catalysts are disclosed in Grubbs et al., Acc. Chem. Res. 1995, 28, 446-452; Yu et al., Nature 2011, 479, 88; and Peryshkov et al., J. Am. Chem. Soc. 2011, 133, 20754.

In some embodiments, the contacting step is performed in a solvent selected from the group consisting of protic solvent, aqueous solvent, organic solvent, and mixtures thereof. For example, the solvent may be chosen from the group consisting of H20, THF, THF/H2O, tBuOH/H20, DMF, DIEA, CH3CN or CH2C12, ClCH2CH2Cl or a mixture thereof. In a particular embodiment, DMF is used.

The peptide is purified and characterized by standard methods.

In a particular embodiment, a method of preparing a peptidomimetic macrocycle according to the invention comprises at least the following steps:
 (i) providing a plurality of peptides comprising protection groups, each peptide being immobilized on a solid support;
 (ii) exposing a deprotection reagent to the immobilized peptides to remove the protection groups from at least a portion of the immobilized peptide;
 (iii) removing at least a portion of the deprotection reagent;
 (iv) solubilizing protected amino acids residues in a solvent, preferably DMF
 (v) using a coupling reagent, preferably HATU,
 (vi) using a base reagent, preferably DIEA
 (vii) exposing protected amino acids residues and coupling reagent to the immobilized peptides such that at least a portion of the activated amino acids residues are bonded to the immobilized peptides to form newly-bonded amino acid residues; and
 (viii) removing at least a portion of activated amino acids residues that do not bond to the immobilized peptides,
 (ix) exposing the final linear polypeptide to Grubb's catalyst reagent for the metathesis reaction generating the peptidomimetic macrocycle,
 (x) exposing the final peptidomimetic macrocycle to cleavage agents for the final deprotection,
 (xi) precipitation, purification and lyophilization of the final peptidomimetic macrocycle, for obtaining preferably a purity of more than 95%.

In the case of preparation of stapled-peptides with lactam bridges, the step (ix) exposing the final linear polypeptide to Grubb's catalyst reagent for the metathesis reaction generating the peptidomimetic macrocycle is replaced by a step (ix)a of deprotection followed by a step (ix)b of cyclization.

Compositions and Combination

Another object of the invention is a pharmaceutical composition comprising at least a peptidomimetic macrocycle as defined above, and a pharmaceutically acceptable carrier.

The pharmaceutical composition can further comprise an adjuvant or additional ingredient. The adjuvant or additional ingredient can enhance the biological activity of the one or more peptides.

In a particular embodiment, the pharmaceutical composition comprises at least a peptidomimetic macrocycle and at least an additional ingredient and/or active selected from the group consisting of anti-inflammatory compounds, anti-metabolites compounds, cellular targeting compounds, preferably macrophages targeting compounds, and/or constituent compounds of liposomes, and mixtures thereof.

As 'anti-inflammatory compounds', mentioned may be made of non steroidal anti-inflammatory drugs (NSAID) and glucocorticoids (steroidal anti-inflammatory drugs).

As 'anti-metabolites compounds', mention may be made of methotrexate used in rheumatoid polyarthritis.

In a particular embodiment, the at least peptidomimetic macrocycle can be provided in a liposome or lipid formulation.

The pharmaceutical composition can be formulated for injection (e.g., intramuscular, subcutaneous, intravenous, or intraperitoneal injection), oral administration, topical administration, transdermal administration, intranasal administration, or inhalation.

In a preferred embodiment, the pharmaceutical composition can be formulated for injection, in particular intravenous injection.

Pharmaceutically acceptable carriers are well known to those skilled in the art and include, for example, sterile saline, lactose, sucrose, calcium phosphate, gelatin, dextrin, agar, pectin, vegetable oils, deionised water and mixtures thereof.

The pharmaceutical composition can comprise one or more stabilizers. For example, the stabilizer can comprise a carbohydrate (e.g., sorbitol, mannitol, starch, sucrose, dextrin, glucose, or a combination thereof), a protein such as albumin or casein, and/or a buffer (e.g., an alkaline phosphate).

Another object of the invention is a combination comprising a peptidomimetic macrocycle as defined above and at least an additional ingredient and/or active as defined above. The peptidomimetic macrocycle and the additional ingredient may be prepared for a simultaneous, sequential or successive use.

The additional ingredient and/or active are defined above.

The peptidomimetic macrocycles provided herein also include pharmaceutically acceptable derivatives or prodrugs thereof.

A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention.

Some pharmaceutically acceptable derivatives include a chemical group which increases aqueous solubility or active transport of the peptidomimetic macrocycle.

The pharmaceutical preparation may be preferably in unit dosage form. The unit dosage form can be a packaged preparation, the package containing discrete quantities of preparation, such as packeted tablets, capsules, and powders in vials or ampoules.

When the compositions of this invention comprise a combination of a peptidomimetic macrocycle and one or more additional therapeutic or prophylactic agents, both the compound and the additional agent should be present at dosage levels of between about 1-100%, and more preferably between about 5-95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections. As an example, the peptidomimetic macrocycle is delivered in a targeted drug delivery system, e.g., in a liposome, preferably a cationic liposome. In a preferred embodiment, the peptidomimetic macrocycle is delivered in a liposome taken up in the mononuclear phagocyte system (MPS) and targeted to the inflamed tissues or organs.

In a particular embodiment, suitable route of administration include intravenous administration.

Uses

The present invention further relates to a peptidomimetic macrocycle as described above, or a pharmaceutical composition or a combination according to the invention, for use as a drug.

In a particular embodiment, the invention relates to a peptidomimetic macrocycle as described above, or a pharmaceutical composition or a combination according to the invention, for use in the prevention or the treatment of inflammation, in particular acute or chronic inflammation.

In a preferred embodiment, the invention relates to a peptidomimetic macrocycle as described above, or a pharmaceutical composition or a combination according to the invention, for use in the prevention or the treatment of acute and chronic inflammatory disorders including infectious or autoimmune diseases, especially tuberculosis, sepsis, meningitis, rheumatoid arthritis, multiple sclerosis, Crohn's disease, of type 2 diabetes, cancer, cardiovascular diseases, or disease caused by pathogenic microorganisms such as bacteria, viruses, parasites or fungi.

Routine of Administration

As illustrated further in the examples, the peptidomimetic macrocycle of the invention are efficient and even have specific efficiency depending of their use in 'simultaneous', 'preventive' or 'curative' conditions.

By 'simultaneous' condition, it means that the peptidomimetic macrocycle of the invention is efficient and even more efficient during the acute phase or chronic phase of an inflammation. The acute phase of an inflammation may be anticipated by detection of markers of inflammation and the peptidomimetic macrocycle of the invention is advantageously used during the acute phase of the inflammation or during a chronic inflammation.

By 'preventive' condition, it means that the peptidomimetic macrocycle of the invention is efficient and even more efficient before the inflammation. The inflammation may be anticipated by detection of markers of inflammation and the peptidomimetic macrocycle of the invention is advantageously used before the said acute phase of inflammation, for example at least 12 hours before, preferably 8 hours before, and in particular 4 hours before the inflammation.

By 'curative' condition, it means that the peptidomimetic macrocycle of the invention is efficient and even more efficient after the diagnosis of an inflammation. The inflammation may be anticipated by detection of markers of inflammation and the peptidomimetic macrocycle of the invention is advantageously used after the beginning of inflammation, for example at least 4 hours after, in particular 8 hours after, and even 12 hours after the inflammation.

So another object of the invention is a peptidomimetic macrocycle of the invention, or a pharmaceutical composition containing it, or a combination of the peptidomimetic macrocycle and an additional ingredient and/or active chosen from the group consisting of anti-inflammatory compounds, cellular targeting compounds, preferably macrophages targeting compounds, and/or constituent compounds of liposomes, and mixtures thereof, for use in the prevention or the treatment of inflammation, in particular acute or chronic inflammation, wherein the peptidomimetic macrocycle is administered before, during and/or after the diagnosis of an inflammatory disorder.

In a particular embodiment, the peptidomimetic macrocycle of 'IRAK2' type of the invention, ie SEQ ID No3 (IRAK2 S1 JMV6645), SEQ ID No4 (IRAK2 S2 JMV6646), and SEQ ID No10 (IRAK2-JM6650) may be used advantageously in simultaneous and/or curative conditions.

In another particular embodiment, the peptidomimetic macrocycle of 'IRAKM' type of the invention, ie SEQ ID No5 (IRAKM S1 JMV6647), SEQ ID No6 (IRAKM S2 JMV6648), and SEQ ID No11 (IRAKM-JM6649) may be used advantageously in simultaneous and/or preventive conditions.

FIGURES

FIG. 1: Scheme of the TRLs pathway

FIG. 2A: Representations of peptidomimetic macrocycles or stapled peptides

FIG. 2B: Representation of the stapled peptides sequences and amino acids positions.

FIG. 3: Inhibition of the endoplasmic reticulum stress by the stapled peptide IRAK2 S1.

Figure 4:
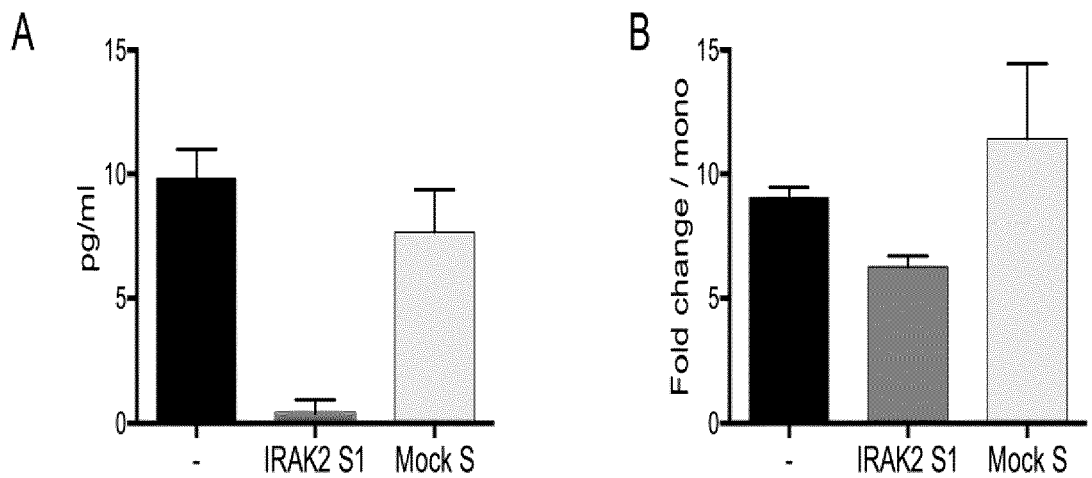

FIG. 4: Inhibition of the induction of IL-1β produced by monocytes during the macrophagic differentiation, by the stapled peptide IRAK2-S1.

FIG. 4A represents the expression level of IL-1β RNA produced by monocytes;

FIG. 4B represents the protein level of IL-1β in the supernatant.

FIG. 5: Inhibition of the LPS induction of the pro-inflammatory cytokines, by the stapled peptides IRAK2-S1 et IRAKM-S1.

FIG. 6: represents three different conditions of LPS stimulation: a condition where LPS stimulation of monocytes and addition of stapled peptides are performed at the same time (simultaneous condition: A), where stapled peptides are added 6 hours before (Preventive condition: B) or 6 hours after (curative condition: C) LPS stimulation.

Figure 7:
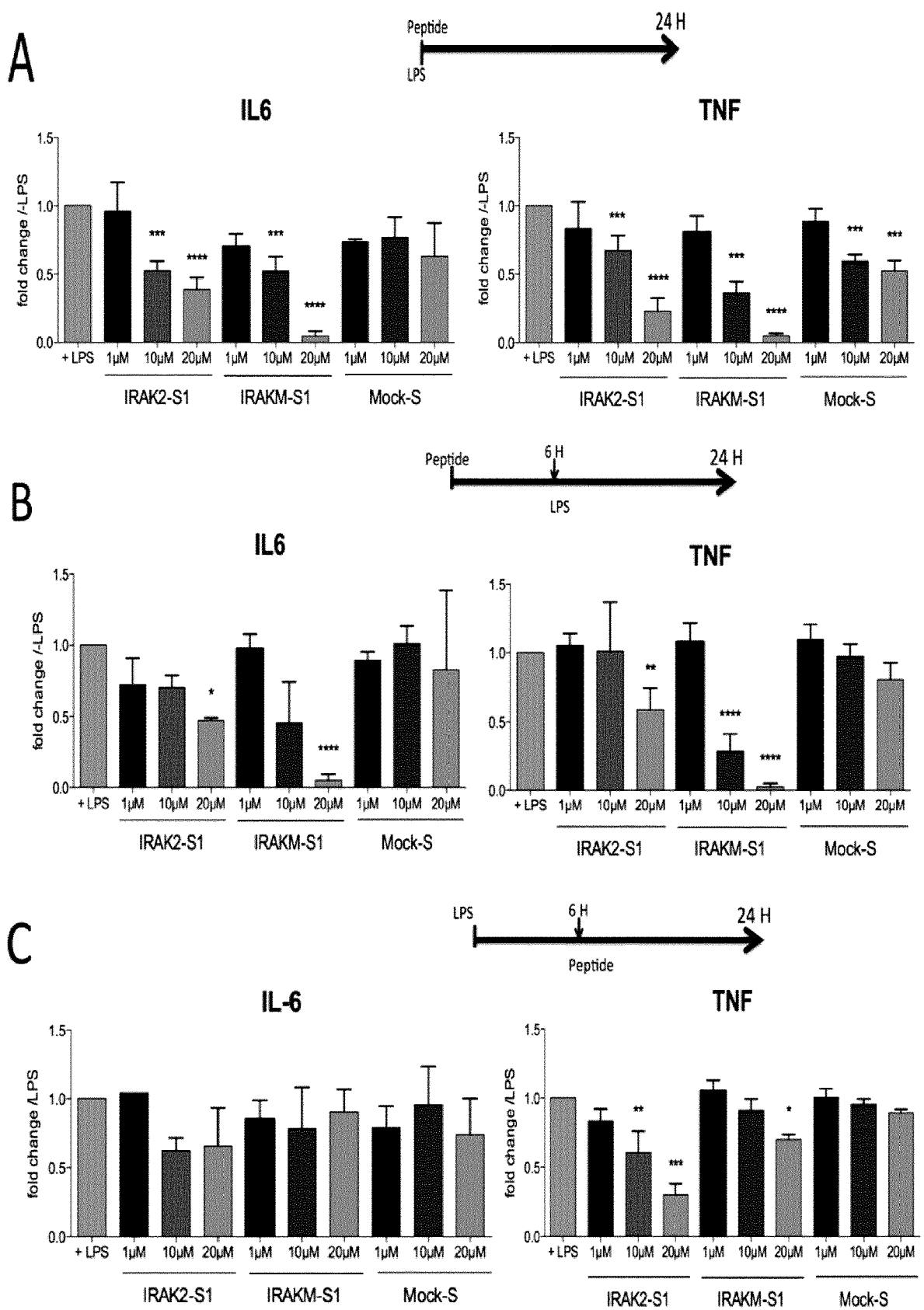

FIG. 7: represents inhibition of IL-6 and TNFα expression following LPS stimulation condition of monocytes with addition of stapled peptides at the same time (simultaneous condition: 7A), 6 hours before (Preventive condition: 7B) or after (curative condition: 7C) LPS stimulation FIG. 8: Evaluation of the stapled-peptides IRAK2-JMV6649 and IRAKM-JMV6650 efficacy on «Simultaneous» condition.

Figure 9:
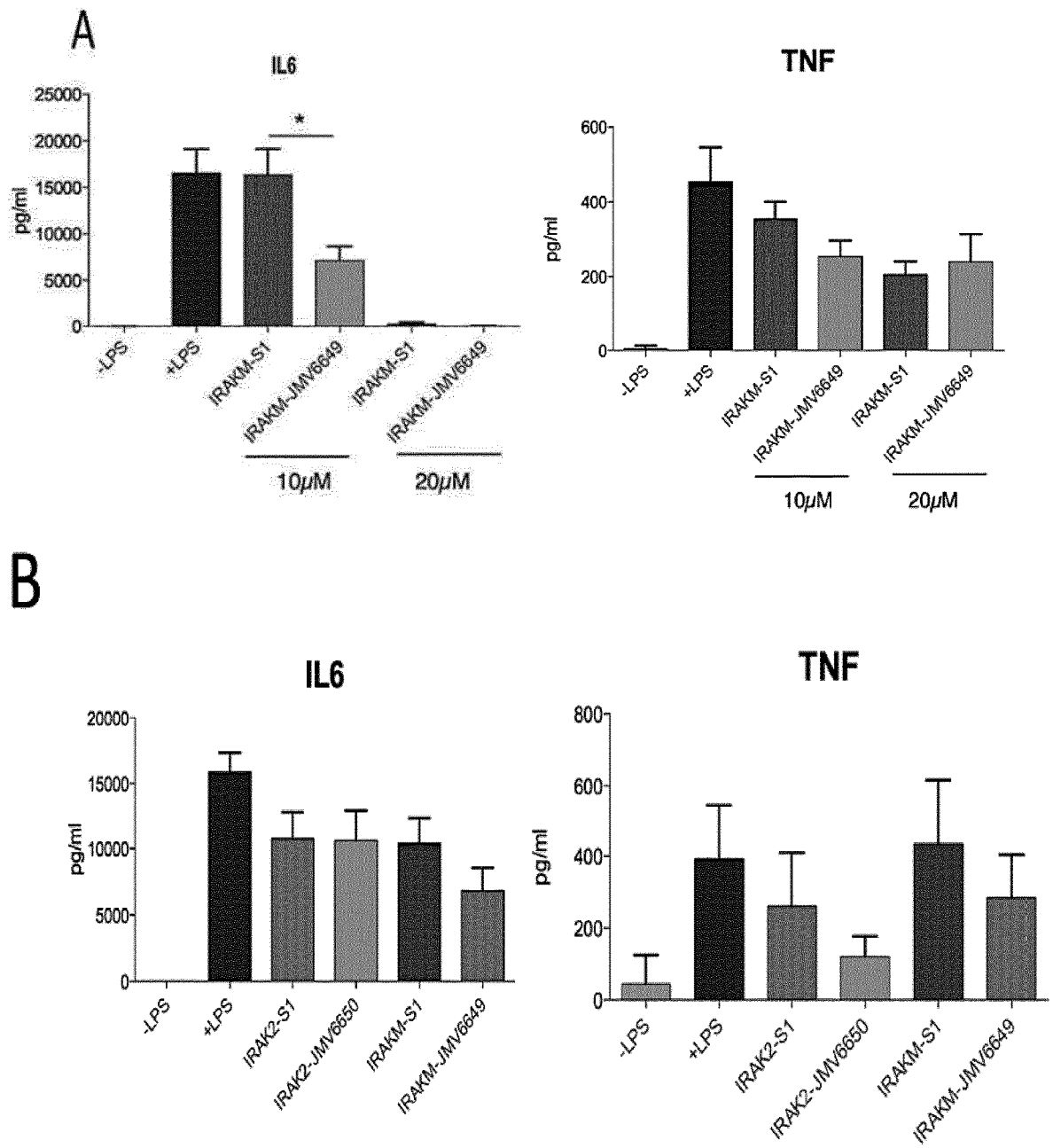

FIG. 9: Evaluation of the new stapled-peptides IRAK2-JMV6649 and IRAKM-JMV6650 efficacicy on «Preventive» condition (9A) and «Curative» condition (9B).

The following non-limiting examples are provided to further illustrate the present invention.

EXAMPLES

Example 1: Preparation and Characterization of Stapled Peptides IRAK2 and IRAKM 1.1 Synthesis of Stapled-Peptides with Hydrocarbon-Bridges The synthesis of the IRAK2 and IRAKM stapled peptides is performed by SPPS methodology manually. The synthesis scale is 0.1 mmol with a 40-RAM amphisphere Rink amide resin loaded at 0.4 mmol/g and an excess of 5 equivalents is used for the protected amino acids. All the protected amino acids as well as the coupling agent O-(7-Azabenzotriazol-1-yl)-N,N,N',N'-tetramethyluronium hexafluorophosphate (HATU) are previously solubilized in DMF to make stock solutions of a concentration of 0.5 M. The resin is initially swollen in 6 ml of DMF for 15 minutes under Vortex agitation. After removal of the DMF by filtration, the deprotection of the Fmoc group is carried out by adding a 20% piperidine/DMF solution (6 ml) with vortexing for 1 minutes. This is done twice. The resin is washed 3 times with DMF. The desired amino acid (1 ml, 0.5 mmol), N, N-diisopropylethylamine (DIEA) (0.164 ml, 1 mmol) and HATU coupling agent (1 ml, 0.5 mmol) are added successively and stirred for 5 minutes under Vortex agitation. This operation is carried out twice with a DMF wash between two couplings. With regard to the amino acid S5 ((S)-a-(2'-pentenyl) alanine), a simple coupling is carried out with a stirring time of 1 hour. This deprotection of the Fmoc and the coupling of the amino acids are repeated until the expected linear sequence is obtained. Once the linear peptide is synthesized, a metathesis reaction is initiated using the first generation Grubbs catalyst (0.04 mmol) in DCE (6 ml) with vortexing for 2 hours. This reaction is carried out twice with a DCM wash between each metathesis reaction.

Once the peptide is stapled, deprotection of the final Fmoc group is carried out and an acetylation reaction is carried out with a solution of acetic anhydride in the presence of DIEA in DMF (1/1/8) for 10 minutes. The final cleavage of the peptide is carried out in the presence of a solution (10 ml) of trifluoroacetic acid, triisopropylsilane and water (95/2.5/2.5). After filtration, the solution is concentrated and taken up in diethyl ether. The precipitate is centrifuged and the mother liquors are decanted. This is done twice. The precipitate is taken up in water and lyophilized to obtain the completely deprotected peptide. Once lyophilized, the peptide is purified on preparative reversed phase HPLC under acetonitrile/water elutions in the presence of 0.1% TFA. The stapled peptide is thus obtained with a purity preferably greater than 95%.

1.2 Synthesis of Stapled-Peptides with lactam-bridges

The synthesis of the IRAK2 and IRAKM lactam peptides is performed by SPPS methodology manually. The synthesis scale is 0.1 mmol with a 40-RAM amphisphere Rink amide resin loaded at 0.4 mmol/g and an excess of 5 equivalents is used for the protected amino acids. All the protected amino acids as well as the coupling agent O-(7-Azabenzotriazol-1-yl)-N,N,N',N'-tetramethyluronium hexafluorophosphate (HATU) are previously solubilized in DMF to make stock solutions of a concentration of 0.5 M. The resin is initially swollen in 6 ml of DMF for 15 minutes under Vortex agitation. After removal of the DMF by filtration, the deprotection of the Fmoc group is carried out by adding a 20% piperidine/DMF solution (6 ml) with vortexing for 1 minutes. This is done twice. The resin is washed 3 times with DMF. The desired amino acid (1 ml, 0.5 mmol), N, N-diisopropylethylamine (DIEA) (0.164 ml, 1 mmol) and HATU coupling agent (1 ml, 0.5 mmol) are added successively and stirred for 5 minutes under Vortex agitation. This operation is carried out twice with a DMF wash between two couplings. With regard to the amino acid fmoc-L-Lys(alloc)-OH and Fmoc-L-Asp(Oall)-OH a simple coupling is carried out with a stirring time of 1 hour. This deprotection of the Fmoc and the coupling of the amino acids are repeated until the expected linear sequence is obtained. Once the linear peptide is synthesized, a deprotection of alloc and allyl is initiated using Tetrakis(triphenylphosphine)palladium(0) (0.04 mmol) with Phenylsilane (2 mmol) in DCM (6 ml) with vortexing for 30 minutes two times. This reaction is carried out twice with a DCM wash between each deprotection reaction. After the deprotection, the lactam is realized with N, N-diisopropylethylamine (DIEA) (0.100 ml, 0.6 mmol) and HATU coupling agent (0.6 ml, 0.3 mmol).

Once the peptide is lactam, deprotection of the final Fmoc group is carried out and an acetylation reaction is carried out with a solution of acetic anhydride in the presence of DIEA in DMF (1/1/8) for 10 minutes. The final cleavage of the peptide is carried out in the presence of a solution (10 ml) of trifluoroacetic acid, triisopropylsilane and water (95/2.5/2.5). After filtration, the solution is concentrated and taken up in diethyl ether. The precipitate is centrifuged and the mother liquors are decanted. This is done twice. The precipitate is taken up in water and lyophilized to obtain the completely deprotected peptide. Once lyophilized, the peptide is purified on preparative reversed phase HPLC under acetonitrile/water elutions in the presence of 0.1% TFA. The stapled peptide is thus obtained with a purity preferably greater than 95%.

1.3 Characterization

Purification of cross-linked compounds was achieved by high performance liquid chromatography (HPLC) (PLC2250, Gilson) on a reverse phase C 18 column (Waters) to yield the pure compounds. Chemical composition of the pure products was confirmed by LC/MS mass spectrometry (Micromass ZQ interfaced with Waters 2790 HPLC system) and amino acid analysis (Beckman System Gold High Performance Liquid Chromatograph). The results are presented in the following Table 3:

TABLE 3

| SEQ ID NO | Sequences | Calculated m/z (M + H) | Calculated m/z (M + 2H) | Observed mass (m/z) |
|---|---|---|---|---|
| 3 | Ac-$S_5$-REL-$S_5$-WWWGBRQA-$NH_2$ | 1892.02 | 947.01 | 947.12 |
| 4 | Ac-RREL-$S_5$-WWW-$S_5$-BRQA-$NH_2$ | 1890.05 | 946.02 | 946.11 |
| 5 | Ac-KSG-$S_5$-REL-$S_5$-WSWAQK-$NH_2$ | 1765.96 | 883.98 | 884.06 |
| 6 | Ac-RREL-$S_5$-WSW-$S_5$-QK-$NH_2$ | 1578.87 | 790.43 | 790.33 |
| 7 | Ac-RRELLWW WGBRQA-$NH_2$ | 1809.99 | 905.99 | 906.06 |
| 8 | Ac-RRELLWSW AQK-$NH_2$ | 1512.83 | 757.41 | 757.42 |
| 9 | Ac-ITF-$S_5$-NLL-$S_5$-YYGP-$NH_2$ | 1490.81 | 746.40 | 746.51 |

TABLE 3-continued

| SEQ ID NO | Sequences | Calculated m/z (M + H) | Calculated m/z (M + 2H) | Observed mass (m/z) |
|---|---|---|---|---|
| 10 | Ac-VSI-S$_5$-REL-S$_5$-WWWGBRQATV-NH$_2$ | 2291.74 | 1146.87 | 1146.97 |
| 11 | Ac-KSG-S$_5$-REL-S$_5$-WSWAQKNKTI-NH$_2$ | 2195.56 | 1098.78 | 1099.05 |
| 12 | Ac-K-REL-D-WWWGBRQA-NH$_2$ | 1767.03 | 884.51 | 884.67 |
| 13 | Ac-VSI-K-REL-D-WWWGBRQATV-NH$_2$ | 2266.64 | 1133.32 | 1133.65 |
| 14 | Ac-KSG-K-REL-D-WSWAQK-NH$_2$ | 1741.98 | 871.99 | 872.16 |
| 15 | Ac-KSG-K-REL-D-WSWAQKNKTI-NH$_2$ | 2198.52 | 1100.26 | 1100.36 |

Example 2: Evaluation of the Specificity and Efficiency of the Stapled Peptides on the IRAK2 Target 2.1. Activation of Endoplasmic Reticulum Stress (ER Stress)

In the cell, the majority of the secreted and membrane proteins are synthesized in the endoplasmic reticulum where they are folded and assembled before being transported. Under certain conditions, proteins of abnormal conformation accumulate in the endoplasmic reticulum (ER), inducing stress (ER stress) and the UPR (unfolded protein response). ER stress also contributes to the inflammatory response by activating the NF-kB transcription factor and the transcription of inflammation genes (pro-inflammatory cytokines) in different ways. The UPR response includes activation of transcription of target genes and deep inhibition of translation, which increases the folding and degradation capabilities and limits the arrival of new proteins in the endoplasmic reticulum. Studies show that the IRAK2 molecule is both essential for the induction of endoplasmic reticulum stress (Benosmab et al. PLoS One 2013) and the anti-viral response mediated by TLR (Toll-like receptor) late phase by interacting directly with IRAK4, replacing IRAK1 (Kawagoe et al., Nature Immunol 2008).

To assess the specificity of recognition of stapled peptides IRAK2, we induced ER stress in human monocytic cell line THP-1 by treatment with tunicamycin (0.1 μg/ml) for 8 h and 24 h.

THP-1 cells were cultured (300 000 cells/well) in RPMI 1640 supplemented with 10% fetal calf serum, 1% penicillin/streptomycin and L-glutamine. The cells were treated with 0.1 μg/ml tunicamycin for 30 min, 8 H or 24 H. The peptide was solubilized in 4% DMSO and used at concentrations ranging from 1 to 20 μM. Total cell RNAs were extracted with the miRNeasy kit (Qiagen), the expression levels of the genes were measured by RT-qPCR with Taqman assays (Lifetechnology) technology.

Figure 1:
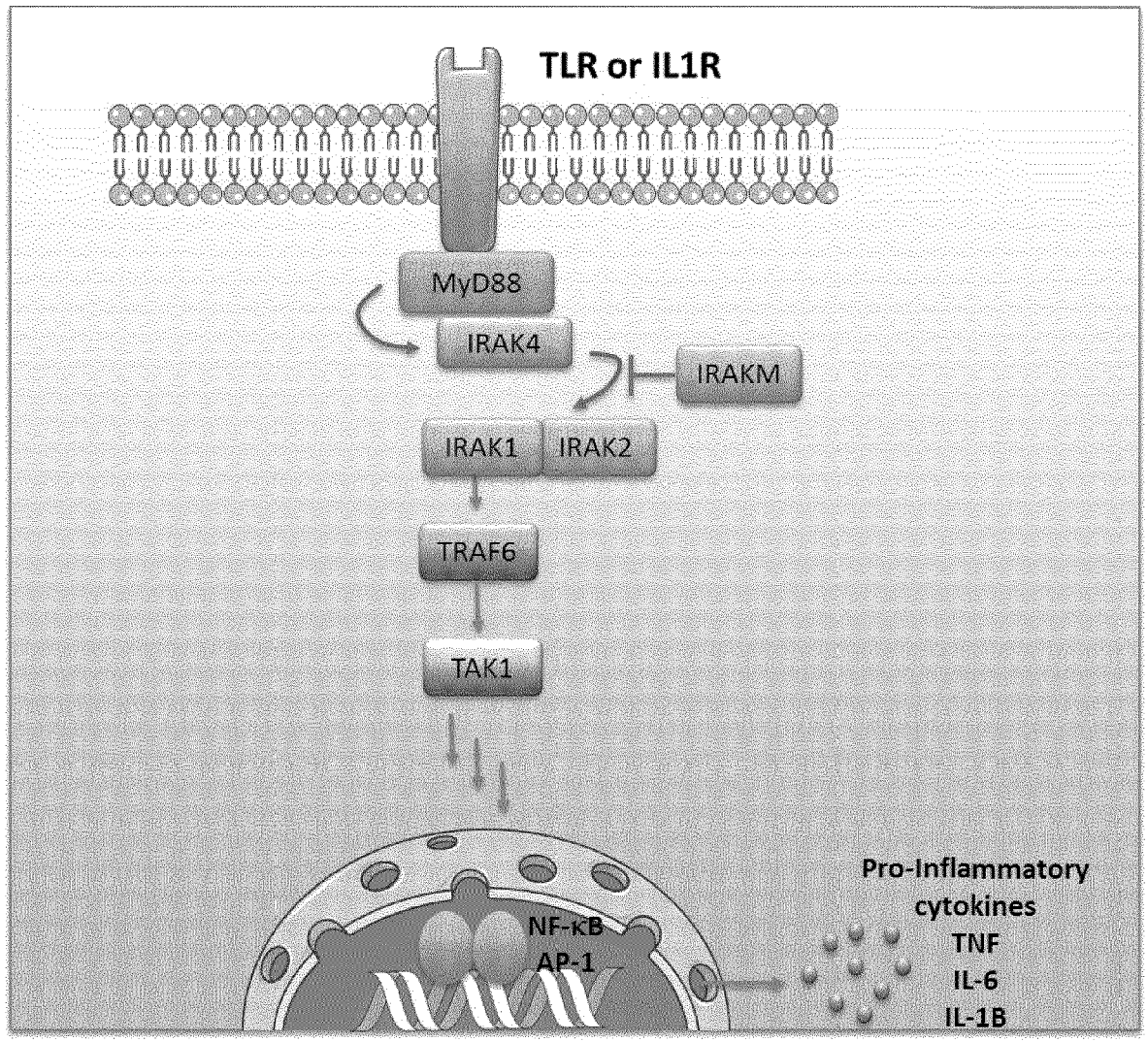
Figure 3:
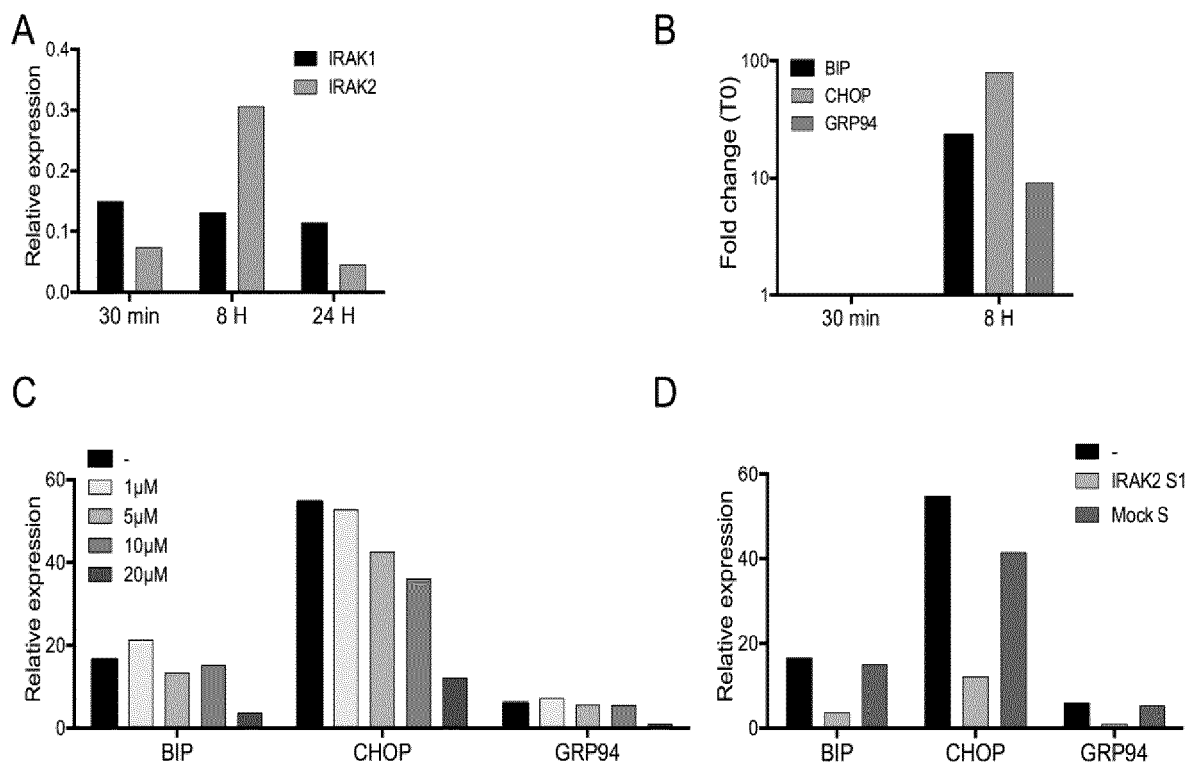
FIG. 3A represents the expression kinetics of RNAs IRAK2 and IRAK1, after treatment with tunicamycin.
FIG. 3B represents the expression of key genes of ER stress.
FIG. 3C represents the dose response effect of IRAK2-S1 peptide on inhibition of gene expression of ER stress.
FIG. 3D represents the specificity of IRAK2-S1 peptide.

We have shown that IRAK2 is the main kinase expressed at 8 h, compared to IRAK1 (FIG. 3A). Measurement of the expression of the CHOP, BIP and GRP94 genes validated the activation of the ER stress at 8H as expected according to literature (FIG. 3B). In this study the peptides IRAK2 Li, IRAKM Li, IRAK2 S1, IRAK2 S2 (Li for linear peptide and S1 and S2 for stapled peptide) were tested. Simultaneous treatment of monocytes with stapled peptide IRAK2 S1 and tunicamycin blocked in a dose-dependent manner the expression of CHOP, GRP94 and BIP, suggesting an inhibition of ER stress (FIG. 3C). This inhibition was specific since, stapled peptide concentration of 20 μM, control stapled peptide (Mock S) has no effect (FIG. 3D). Our results suggest that the IRAK2-S1 stapled peptide interacts specifically with IRAK4 and inhibits its activating effect of ER stress.

2.2 Induction of Macrophage Differentiation.

The stimulation of the monocytes THP-1 by PMA (Phorbol-12-myristate-13-acetate) induces their differentiation in macrophages. This is associated with an induction of the expression of certain TLRs (2 and 4), members of the IRAK family, activation of the NF-kB pathway and secretion of the pro-inflammatory cytokine IL-1β. Using RNA against interference IRAK1, IRAK2 and IRAK4, previous work showed the decrease in expression of IL-1β, at both the mRNA and protein levels (Tiwari et al, Journal of Immunology 2011).

We stimulated the THP-1 monocytes with 0.1 μg/ml PMA for 48 h to induce differentiation into macrophages, and treated with 20 μM stapled peptide (IRAK2-S1 or Mock-S).

THP1 cells were cultured (300,000 cells/well) in RPMI 1640 supplemented with 10% fetal calf serum, 1% penicillin/streptomycin and L-glutamine. The cells were treated with 0.1 μg/ml of PMA for 48 h. The peptides were solubilized in 4% DMSO and used at 20 μM. The peptides are added together with the PMA. Total RNA of the cells were extracted by the miRNeasy kit (Qiagen), the level of expression of IL-1β was measured by RT-qPCR technology by Taqman assays (lifetechnology)

After extraction of the RNAs, we quantified by RT-qPCR the level of expression of the RNA of IL-1β (FIG. 4A). Using ELISA method, the cytokine secretion was measured in the supernatant of the treated THP-1 (FIG. 4B). The IRAK2-S1 peptide was able to block the expression and production of IL-1β at 20 μM. At this concentration, the peptide appears to have no effect on viability and morphology of the cells.

2.3 Induction of the Response to Endotoxin.

Inflammation is a complex physiological state adopted primarily by innate immune cells in response to infection and/or tissue damage. Adaptations exist to regulate an over-inflammation and function as a protection of the host against endotoxin shocks. One of the classic examples of such a protection mechanism is endotoxin tolerance. A phenomenon in which cells or organisms exposed to low concentrations of endotoxins (LPS) enter a state of transient hypo-response being unable to respond to new stimulations by endotoxin; in other words, they develop a kind of "tolerance" to endotoxin. This phenomenon has been observed both in vitro on monocytes and macrophages and in vivo in animal models as well as in humans (Biswas SK et al., Trends in Immunology, 2009). Under tolerance conditions, IRAK-M (or IRAK-3) is over expressed in monocytes (Escoll et al, BBRC, 2003) and negatively regulates the activation of Toll-like receptor-dependent MyD88 (TLR2, TLR4, TLR7/8, and TLR9). The hypo response in the in vitro THP-1 model of tolerance to LPS, is characterized by reduced expression of TNFα and IL-6 after two consecutive stimulations of LPS, a first dose at low concentrations, followed by a strong dose 18 hours apart. Stapled peptides mimicking the action of the natural Myddosome inhibitor IRAK-M, the exposure of monocytes to THP1 stapled IRAK-2 peptide is expected to reproduce the conditions of LPS-tolerance.

THP1 cells were cultured (300 000 cells/well) in RPMI 1640 supplemented with 10% fetal calf serum, 1% penicillin/streptomycin and L-glutamine. The cells were treated with 0.1 µg/ml LPS for 6 h for TNFα, and 24 h for IL-6 and IL-1β. The peptides were solubilized in 4% DMSO and used at 5 and 20 µM. The peptides were added at the same time as the LPS. The determination of the cytokines in the culture supernatants was carried out with the specific ELISA kits (eBioscience).

FIG. 5 shows the ELISA assays of IL-1β, TNFα and IL-6 pro-inflammatory cytokines secreted by THP1 cells after LPS stimulation (0.1 µg/ml). Treatment of cells by the stapled peptide IRAK2-S1 reduced the expression of the 3 cytokines in a dose-dependent manner (FIG. 5A). Treatment of the THP-1 with the stapled peptide IRAKM-S1 having 50% sequence homology with IRAK2-S1 produced a similar action of inhibiting the expression of the 3 cytokines (FIG. 5B).

These different functional studies show that the stapled peptides according to the invention are modulators of the TLR pathway by inhibiting the MyD88/IRAK4/IRAK2 complex, leading to decreased production of TNFα, IL-6 and IL-1b pro-inflammatory cytokines.

Example 3: Evaluation of the Stapled-Peptides IRAK2-S1 and IRAK-M-S1 Efficacy Following Three Different Conditions: Simultaneous, Curative, or Preventive Treatment The previous examples show that stapled-peptides mimic the action of the natural mydosome inhibitor IRAK-M. Indeed, it is demonstrated that the exposure of THP1 monocytes to the stapled-peptides IRAK2-S1 and IRAKM-S1 six hours after LPS stimulation reproduced the LPS tolerance conditions, i.e. inhibition of IL-6 and TNFα cytokine production. The present example studies whether different experimental settings are able to reveal better efficacy. Three different conditions of LPS stimulation were compared: a condition where LPS stimulation of monocytes and addition of stapled peptides are performed at the same time (simultaneous condition: A), where stapled peptides are added 6 hours before (Preventive condition: B) or 6 hours after (curative condition: C) LPS stimulation (FIG. 6).

For all conditions tested, THP-1 monocytes were cultured (300 000 cells/well) in RPMI with 10% fetal calf serum; 1% penicillin/streptomycin and L-glutamine. THP-1 were treated with 0.1 µg/mL of LPS for 24 hours, stapled-peptides IRAK2-S1 et IRAKM-S1 were used at 1 to 20 µM and added at the same time for condition A, 6 hours before LPS for condition B and 6 hours after LPS for condition C. The quantification of cytokine in the culture supernatants was carried out with specific IL-6 and TNFα ELISA (eBioscience).

The results are represented in FIG. 7 and disclosed hereunder:

«Simultaneous» condition (7A): Dose-response inhibition of TNFα and IL-6 expression was observed for the two peptides tested. The peptides IRAK2-S1 and IRAKM-S1 significantly inhibit the secretion of TNFα and IL-6 cytokines at 10 and 20 µM, with a greater effect for the IRAKM-S1 at 20 µM, which inhibits up to 95% and 90% of TNFα and IL-6 expression, respectively. However, at this concentration, the peptide Mock-S control induces non-specific inhibition of TNFα and IL-6 in the range of 15 to 20% (FIG. 7A). IRAKM-S1 appears to be more efficient than IRAK2-S1 to reduce pro-inflammatory cytokine production by monocytes.

«Preventive» Condition (7B): Dose-response inhibition of TNFα and IL-6 expression level was observed for IRAKM-S1, which significantly inhibits the secretion of TNFα (95%) and IL-6 (90%) at 20 µM. At this concentration, IRAK2-S1 inhibits TNFα and 11-6 expression by only 15 to 20%. No inhibition of cytokine expression was observed at 10 µM for IRAK2-S1 (FIG. 7B). Unlike IRAK2-S1, the stapled peptide IRAKM-S1 displayed a preventive effect on the expression of pro-inflammatory cytokines in THP-1 monocytes after TLR4 engagement.

«Curative» Condition (7C): Dose-response inhibition of TNFα expression level was observed for IRAK2-S1, which significantly inhibits TNFα secretion yp to 30% and 70% at 10 and 20 µM, respectively. At 20 µM, IRAKM-S1 inhibits TNFα expression by only 15 to 20%. No inhibition of cytokine expression was observed at 10 µM for IRAKM-S1 (FIG. 7C). Finally, no effect on the expression level of IL-6 was observed for this condition for both stapled peptides (FIG. 7C). Unlike IRAKM-S1, the stapled peptide IRAK2-S1 displayed a curative effect on the expression of TNFα in THP-1 monocytes following TLR4 engagement.

These results demonstrated that IRAKM-S1 is more efficient in simultaneous and preventive conditions than in curative condition. IRAK2-S1 is more efficient in simultaneous and curative conditions than in preventive condition. The man skilled in the art will be able to adapt the routine of administration of the said stapled peptides, taken into account the condition and/or disorder to be treated, and based on the efficiency and behavior of each stapled-peptide.

Example 4: Evaluation of New Stapled Peptides IRAK2-JMV6649 and IRAKM-JMV6650

In vitro efficacy of the new stapled-peptides IRAK2-JMV6649 and IRAKM-JMV6650 for matching to natural sequences of IRAK2 54-71 and IRAKM 66-83 was evaluated and compared with IRAK2-S1 and IRAK-M-S1 under three different conditions: simultaneous, curative, and preventive treatment.

For all conditions tested, THP-1 monocytes were cultured (300 000 cells/well) in RPMI with 10% fetal calf serum; 1% penicillin/streptomycin and L-glutamine. THP-1 were treated with 0.1 µg/mL of LPS for 24 hours, stapled-peptides IRAK2-S1, IRAK2-JMV6649, IRAKM-S1 and IRAKM-JMV6650 were used at 10 to 20 µM and added at the same time for «Simultaneous» condition, 6 hours before LPS for «preventive» condition and 6 hours after LPS for «curative» condition. Using ELISA (eBioscience), IL-6 and TNFα quantification was carried out in monocyte culture supernatants.

The results for the "simultaneous" condition are presented in FIG. 8 and disclosed hereunder:

«Simultaneous» condition: at 20 µM, IRAKM-JMV6649 decreases by more than 70% the secretion of IL-6, compared with the peptide IRAKM-S1, but displayed no additive inhibitory effect on TNFα expression (FIG. 8A). No more efficacy of the IRAK2 peptide was observed with the JMV6650 modification (FIG. 8B).

The results for the "preventive" and "curative" conditions are presented in FIG. 9 and disclosed hereunder:

«Preventive» condition: IRAKM-JMV6649 peptide induces a better inhibition of the IL-6 expression than the IRAKM-S1 peptide with an additional inhibition of 60% at 10 µM and 80% at 20 µM. Inhibition of TNFα expression is greater with the modified peptide IRAKM-JMV6649, reaching 20% at 10 μM. (FIG. 9A). No more efficacy of IRAK2 peptide was observed with JMV6650 modification (data not shown).

«Curative» condition: New peptides showed no significant additional inhibition on cytokine expressions. Although IRAK2-JMV6650 tends to decrease TNFα production more efficiently than IRAK2-S1, it was not significant, and it acts as IRAK2-S1 at 20 μM on IL-6 expression. IRAKM-JMV6649 has a tendency to increase the inhibition of TNFα and IL6 expression at 20 μM compared to IRAKM-S1, but again it was not significant (FIG. 9B).

These results demonstrated that chemical modifications on IRAKM peptide sequence provide a benefit for the inhibition of IL-6 expression by monocytes under «simultaneous» and «preventive» condition treatment. While those brought to the sequence of IRAK2 peptide did not bring any significant benefit in all treatment conditions tested.

All these results demonstrated that the stapled-peptides according to the invention are efficient but with specificities of behavior, ie some of them are more efficient in preventive condition (before the diagnosis of an inflammation), and/or more efficient in simultaneous condition (during the inflammation), and/or more efficient in curative condition (after the diagnosis of an inflammation). The stapled peptides IRAK2-JMV6650 and IRAKM-JMV6649 are as efficient as IRAK2-S1 or IRAKM-S1 showing that modifications on their Ac and $NH_2$ terminations for matching to the natural sequences of IRAK2 54-71 and IRAKM 66-83 do not impact their efficiency

The invention claimed is:

1. A peptidomimetic macrocycle having from 8 to 30 amino adds comprising at least one macrocycle-forming linker and an amino add sequence chosen from the group consisting of:
   (i) an amino add sequence with at least 50%, 60%, 70%, 80%, 90%, or 95% sequence identity to human sequence IRAK2 54-71 (SEQ ID NO:1) and 100% identity with the amino adds in the positions 5-6, 9-11, and 14-15; and
   (ii) an amino add sequence with at least 50%, 60%, 70, 80%, 90%, or 95% sequence identity to human sequence IRAKM 66-83 (SEQ ID NO:2) and 100% identity with the amino adds in the positions 5-6, 9-11, and 13-14, wherein the peptidomimetic macrocycle comprises an α-helix and at least two natural or non-natural amino adds cross-linked by the macrocycle-forming linker at i and i+3 positions, i and i+4 positions, or i and i+7 positions.

2. A peptidomimetic macrocycle according to claim 1, wherein the macrocycle-forming linker comprises a saturated hydrocarbon chain or an unsaturated hydrocarbon chain.

3. A peptidomimetic macrocycle according to claim 2, wherein the macrocycle-forming linker comprises a hydrocarbon chain chosen from the group consisting of alkylene, alkenylene, alkynylene, or a derivative thereof.

4. A peptidomimetic macrocycle according to claim 2, wherein a —$CH_2$— group of said hydrocarbon chain has been replaced with an amide function —NH—CO—.

5. A peptidomimetic macrocycle according to claim 1, wherein the two natural or non-natural amino adds cross-linked by a macrocycle-forming linker are at i and i+4 positions.

6. A peptidomimetic macrocycle according to claim 1, comprising an amino add sequence chosen from the group consisting of:

```
SEQ ID NO: 3 (IRAK2 S1):
Ac-X-REL-X-WWWGBRQA-NH2,

SEQ ID NO: 4 (IRAK2 S2):
Ac-RREL-X-WWW-X-BRQA-NH2,

SEQ ID NO: 5 (IRAKM S1):
Ac-KSG-X-REL-X-WSWAQK-NH2,

SEQ ID NO: 6 (IRAKM S2):
Ac-RREL-X-WSW-X-QK-NH2,

SEQ ID NO: 10 (IRAK2-JMV6650)
Ac-VSI-X-REL-X-WWWGBRQA-NH2,
and

SEQ ID NO: 11 (IRAKM-JMV6649)
Ac-KSG-X-REL-X-WSWAQKNKTI-NH2,
``` wherein "X" represents a non-natural a non-natural amino acid that is derivatized with olefins which are cross-linked to form a macrocycle-forming linker, and "B" represents norleucine; or

```
SEQ ID NO: 12 (IRAK2-JMV6651):
Ac-K-REL-D-WWWGBRQA-NH2,

SEQ ID NO: 13 (IRAK2-JMV6652):
Ac-VSI-K-REL-D-WWWGBRQATV-NH2,

SEQ ID NO: 14 (IRAKM-JMV6653):
Ac-KSG-K-REL-D-WSWAQK-NH2,
and

SEQ ID NO: 15 (IRAKM-JMV6654):
Ac-KSG-K-REL-D-WSWAQKNKTI-NH2,
``` wherein natural amino adds lysine (K) and aspartic add (D) are cross-linked to form the macrocycle-forming linker, and "B" represents norleucine.

7. A peptidomimetic macrocycle according to claim 6, wherein the non-natural amino add "X" is (S)-2-(4'-pentenyl)alanine or a derivative thereof.

8. A peptidomimetic macrocycle according to claim 1, further comprising at least one spacer.

9. A peptidomimetic macrocycle according to claim 1, further comprising at least one cell-penetrating peptide.

10. A peptidomimetic macrocycle according to claim 1, wherein the peptidomimetic macrocycle is administered before, during, and/or after the diagnosis of an inflammatory disorder.

11. A pharmaceutical composition comprising at least a peptidomimetic macrocycle as defined in claim 1 and at least one pharmaceutically acceptable carrier.

12. A pharmaceutical composition according to claim 11, wherein said composition is administered before, during, and/or after the diagnosis of an inflammatory disorder.

13. A pharmaceutical composition according to claim 11, further comprising an additional ingredient and/or active chosen from the group consisting of anti-inflammatory compounds, cellular targeting compounds, constituent compounds of liposomes, and mixtures thereof.

14. A method for inhibiting or treating inflammation comprising the administration of an effective amount of a peptidomimetic macrocycle according to claim 1 to a patient in need thereof.

15. A method according to claim 14, wherein said inflammation results from an infectious disease, an autoimmune disease, or a disease caused by pathogenic microorganisms.

16. A method according to claim 15, wherein said inflammation results from tuberculosis, sepsis, meningitis, rheumatoid arthritis, multiple sclerosis, Crohn's disease, type 2 diabetes, cancer, cardiovascular disease, a disease caused by bacteria, a disease caused by viruses, a disease caused by parasites, or a disease caused by fungi.

17. A method for inhibiting or treating inflammation comprising the administration of an effective amount of a pharmaceutical composition according to claim 11 to a patient in need thereof.

18. A method according to claim 17, wherein said inflammation results from an infectious disease, an autoimmune disease, or a disease caused by pathogenic microorganisms.

19. A method according to claim 18, wherein said inflammation results from tuberculosis, sepsis, meningitis, rheumatoid arthritis, multiple sclerosis, Crohn's disease, type 2 diabetes, cancer, cardiovascular disease, a disease caused by bacteria, a disease caused by viruses, a disease caused by parasites, or a disease caused by fungi.

* * * * *